US012754180B2

(12) United States Patent
Sherbenou et al.

(10) Patent No.: US 12,754,180 B2
(45) Date of Patent: Oct. 6, 2026

(54) MONOCLONAL ANTIBODY DRUG SENSITIVITY IN MULTIPLE MYELOMA PATIENTS

(71) Applicant: The Regents of the University of Colorado, a body corporation, Denver, CO (US)

(72) Inventors: Daniel Sherbenou, Denver, CO (US); Zachary Walker, Aurora, CO (US); Michael Vanwyngarden, Aurora, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 872 days.

(21) Appl. No.: 17/298,646

(22) PCT Filed: Dec. 2, 2019

(86) PCT No.: PCT/US2019/063977
§ 371 (c)(1),
(2) Date: May 31, 2021

(87) PCT Pub. No.: WO2020/113210
PCT Pub. Date: Jun. 4, 2020

(65) Prior Publication Data

US 2022/0003750 A1 Jan. 6, 2022

Related U.S. Application Data

(60) Provisional application No. 62/774,177, filed on Dec. 1, 2018.

(51) Int. Cl.
*G01N 33/50* (2006.01)
*C12N 5/078* (2010.01)

(52) U.S. Cl.
CPC ....... *G01N 33/5011* (2013.01); *C12N 5/0634* (2013.01); *C12N 2501/2306* (2013.01); *C12N 2503/02* (2013.01); *G01N 2333/70589* (2013.01); *G01N 2333/70596* (2013.01)

(58) Field of Classification Search
CPC .............. G01N 33/5011; C12N 5/0634; C12N 2501/2306
USPC .......................................................... 435/7.23
See application file for complete search history.

(56) References Cited

U.S. PATENT DOCUMENTS

2012/0316137 A1* 12/2012 Huang ................. C07D 487/04 514/249
2017/0356911 A1* 12/2017 Superti-Furga ........ C12M 23/20

FOREIGN PATENT DOCUMENTS

CN 105603087 A * 5/2016
WO WO-2015181303 A1 * 12/2015 ............... C12N 9/50
WO WO-2018064440 A1 * 4/2018 ............ C12M 29/10
WO WO-2018089928 A1 * 5/2018 .............. A61P 19/06

OTHER PUBLICATIONS

Perfetto et al., Amine-Reactive Dyes for Dead Cell Discrimination in Fixed Samples, (2010), Current Protocols in Cytometry 9.34.1-9.34.14, Jul. 2010. (Year: 2010).*
Kovář et al., Serum-Free Medium for Hybridoma and Parental Myeloma Cell Cultivation, Methods in Enzymology, vol. 121, 277-292 . (Year: 1984).*
StemCell Technologies, BIT 9500 Serum Substitute, Catalog# 09500, 2017. (Year: 2017).*
Barwick et al., Cell of Origin and Genetic Alterations in the Pathogenesis of Multiple Myeloma, Frontiers in Immunology, vol. 10, 1-17. (Year: 2019).*

* cited by examiner

*Primary Examiner* — Gregory S Emch
*Assistant Examiner* — Omar Ramadan
(74) *Attorney, Agent, or Firm* — Sheridan Ross P.C.

(57) ABSTRACT

An ex vivo method of determining sensitivity of multiple myeloma cells obtained from a multiple myeloma patient to chemotherapeutic agents, and methods of specifically treating the patient with chemotherapeutic agents to which the multiple myeloma cells are sensitive.

17 Claims, 20 Drawing Sheets

| Group | Pt# | LOT | Bor | Car | Len | Pom | Dex | Cy |
|---|---|---|---|---|---|---|---|---|
| Newly Diagnosed | 134 | 0 | 5 | 1 | 95 | 84 | 129 | 96 |
| | 576 | 0 | 35 | 42 | 48 | 74 | 70 | 116 |
| | 616 | 0 | 2 | 0 | 88 | 54 | 19 | 88 |
| | 656 | 0 | 13 | 17 | 31 | 40 | 51 | 45 |
| | 748 | 0 | 45 | 74 | 88 | 76 | 81 | 67 |
| | 766 | 0 | 64 | 27 | 74 | 103 | 76 | X |
| | 820 | 0 | 56 | 11 | 16 | 34 | 105 | 121 |
| | 829 | 0 | 91 | 87 | 74 | 83 | 70 | 113 |
| | 839 | 0 | 47 | 87 | 87 | 108 | 120 | 35 |
| | 847 | 0 | 15 | 5 | 81 | 96 | 39 | 52 |
| | 854 | 0 | 7 | 26 | 71 | 88 | 42 | 65 |
| | 897 | 0 | 46 | 74 | 38 | 40 | 84 | 72 |
| | 916 | 0 | 10 | 42 | 62 | 52 | 72 | 11 |
| | 1003 | 0 | 14 | 30 | 82 | 85 | 84 | 63 |
| | 1010 | 0 | 23 | 60 | 52 | 68 | 61 | 12 |
| | 1023 | 0 | 73 | 88 | 76 | 84 | 74 | 70 |
| | 1064 | 0 | 10 | 21 | 42 | 43 | 33 | 26 |
| | 1093 | 0 | 52 | 58 | 103 | 75 | 86 | 36 |
| | 1115 | 0 | 90 | 91 | 71 | 68 | 74 | 81 |
| | 1128 | 0 | 64 | 39 | 91 | 69 | 90 | 110 |
| | 1229 | 0 | 48 | 48 | 73 | 71 | 95 | 70 |
| | 1230 | 0 | 25 | 91 | 93 | 82 | 70 | 95 |
| | 1238 | 0 | 56 | 90 | 94 | 81 | 138 | 77 |
| | 1298 | 0 | 64 | 32 | 58 | 52 | 76 | 74 |
| First Relapse | 134 | 1 | 59 | 81 | 66 | 83 | 106 | 100 |
| | 576 | 1 | 45 | 50 | 108 | 119 | 115 | 55 |
| | 678 | 1 | 9 | 0 | 31 | 39 | 74 | 21 |
| | 700 | 1 | 94 | 74 | 73 | 72 | 145 | 70 |
| | 951 | 1 | 65 | 88 | 68 | 69 | 79 | 51 |
| | 1270 | 1 | 13 | 46 | 63 | 48 | 53 | 18 |
| | 420 | 2 | 21 | 2 | 47 | 61 | 30 | 37 |
| | 614 | 2 | 24 | 13 | 55 | 52 | X | X |
| | 649 | 2 | 93 | 69 | 102 | 90 | 74 | 50 |
| | 875 | 2 | 51 | 13 | 109 | 143 | 61 | 97 |
| | 994 | 2 | 36 | 45 | 60 | 49 | 109 | 39 |
| | 1196 | 2 | 106 | 98 | 97 | 98 | 77 | 93 |
| Multi-Relapsed | 573 | 2 | 26 | 72 | 73 | 68 | 58 | 71 |
| | 700 | 2 | 87 | 99 | 116 | 89 | 81 | 41 |
| | 1044 | 2 | 35 | 53 | 65 | 67 | 53 | 33 |
| | 1322 | 2 | 72 | 96 | 83 | 88 | 97 | 116 |
| | 750 | 3 | 54 | 47 | 78 | 97 | 18 | 28 |
| | 816 | 3 | 11 | 19 | 73 | 68 | 90 | 58 |
| | 955 | 3 | 55 | 75 | 79 | 65 | 71 | 68 |
| | 1123 | 3 | 65 | 74 | 95 | 85 | 104 | 22 |
| | 1310 | 3 | 54 | 87 | 83 | 102 | 102 | 93 |
| | 614 | 4 | 27 | 96 | 79 | 65 | 90 | 50 |
| | 634 | 4 | 11 | 4 | 96 | 110 | X | X |
| | 646 | 4 | 49 | 112 | 83 | 117 | 78 | 81 |
| | 649 | 4 | 82 | 79 | 81 | 86 | 94 | 49 |
| | 1070 | 4 | 30 | 44 | 104 | 83 | 64 | 36 |
| | 634 | 5 | 38 | 25 | 140 | 121 | 154 | 167 |
| | 611 | 5 | 111 | 72 | 125 | 116 | 98 | 75 |
| | 646 | 5 | 81 | 94 | 90 | 98 | 69 | 89 |
| | 675 | 5 | 118 | 117 | 95 | 86 | 127 | 123 |
| | 634 | 6 | 47 | 83 | 87 | 86 | 15 | 97 |

Viable MM Cells (Norm %): 0, 20, 40, 60, 80

FIG. 3A

MONOCLONAL ANTIBODY DRUG SENSITIVITY IN MULTIPLE MYELOMA PATIENTS

CROSS-REFERENCE TO RELATED APPLICATIONS

This application claims priority to U.S. Provisional Application No. 62/774,177, filed Dec. 1, 2018, the disclosure of which is hereby incorporated by reference in its entirety.

FIELD

This disclosure relates generally to the field of personalized cancer treatments for multiple myeloma patients.

BACKGROUND

Multiple myeloma (MM) is a mostly incurable blood cancer that has been consistently increasing in incidence. In the 2000s, the life expectancy of patients with MM greatly improved with the implementation of proteasome inhibitors (PIs; e.g., bortezomib and carfilzomib) and immunomodulatory drugs (IMiDs; e.g., lenalidomide and pomalidomide). The use of these agents now predominates both upfront and relapsed settings. In addition, the monoclonal antibody daratumumab (Dara) has emerged as an essential agent in the treatment of relapsed disease, and it has started to move into the upfront setting as well. Despite this progress, all patients' disease inevitably becomes drug resistant, and quality of life is adversely affected by lytic bone lesions, pathologic fractures, renal failure, immune compromise, and eventually death. Although new therapies continue to emerge, there has been little coinciding progress in developing biomarkers that would allow the personalization of treatment choices.

As recognition of the diversity of genetic drivers among each pathologically defined hematologic malignancy has increased, the need for personalizing cancer treatments has become clear. In myeloma, implementing personalized medicine has been challenging due to the extensive genetic heterogeneity underlying the disease. Nearly one-half of patients have translocations that juxtapose the heavy chain promoter with various oncogenes, and the other half have an increased number of odd-numbered chromosomes (known as hyperdiploidy). The specific oncogenes overexpressed or dysregulated from IGH translocations include cyclin D1, cyclin D3, MMSET/FGFR, C-MAF and MAFB, each of which has been difficult to successfully target in MM. Similarly, the tumor suppressors and oncogenes most commonly aberrant, TP53, K-RAS and N-RAS, are also notoriously hard to target. A minority of patients develop mutations in druggable proteins, including B-RAF and IDH1, but the potential benefits of targeted inhibition of these in myeloma has not yet been established. In contrast, many drugs have been successfully developed that target common phenotypic features of myeloma.

Targeting common aspects of myeloma cell biology has translated directly into clinical benefit. There are currently more than fifteen clinically used drugs for MM in at least six different drug classes. Among each of the drug classes, cross-resistance between agents is variable and unpredictable from patient-to-patient. Despite great progress in drug development, none of the current agents have led to cures for the majority of patients. As a result, myeloma is now managed much like a chronic disease, with patients more frequently on therapy than off Through its oft turbulent course, patients are cycled empirically through multiple lines of therapy typically consisting of 2-3 drug combinations. Dexamethasone (Dex) is part of almost all combinations used, regardless of a patient's prior exposure. The exact sequence of drug regimens chosen is highly variable and heavily influenced by individual physician preference. As a result, there is inconsistency in clinical practice, and patient outcomes are disparate across care delivery settings.

Currently, variability in the clinical approach to myeloma treatment progressively increases from diagnosis to refractory disease. In the frontline setting, 3-drug induction combinations are favored over 2-drug combinations for fit patients. Three drug combinations have rarely been compared head to head, but recently a PI, IMiD and Dex combination was found to have similar, but slightly better depth of response than another popular combination with cyclophosphamide (Cy), PI and Dex. In addition, 4-drug combinations including Dara are further increasing the complexity of options available. As a maintenance treatment, lenalidomide (Len) improves survival, but other anti-myeloma drugs do not yet have supportive evidence in this setting. At the time of first relapse, several combinations can be appropriately used, including daratumumab, carfilzomib or elotuzumab-based regimens. Clinical decision-making in the multi-relapsed setting is even more variable, with increasing guesswork and decreasing response rates with increasing number of prior treatment lines. Inevitably, resistance develops to the available drugs. When multi-drug resistant disease arises, the prognosis becomes very poor. The clinical determination of whether a patient is resistant to individual agents is often difficult, as PIs, IMiDs, steroids, chemotherapy and monoclonal antibodies are used in complex sequences of combination regimens.

Thus, there is a need for a short-term, ex vivo cell culture methodology of measuring multiple myeloma patient sensitivity to available chemotherapeutic agents with a reasonable turnaround time for clinical use.

SUMMARY

The present inventors have optimized the viability of primary myeloma cells to provide added data to clinicians on individual patient drug sensitivity, using a short-term cell culture approach for ex vivo drug sensitivity profiling of clinically available agents. This testing approach is performed by culturing patient bone marrow (BM) aspirate mononuclear cells (MNCs) with one or more of Bor, Car, Len, Pom, Cy, Dex, and Dara, followed by high-throughput flow cytometry after 48 hours to measure the surviving MM cell population. This approach was tested in patient BM samples pretreatment, and at progressive rounds of MM recurrence/relapse. Recapitulating the clinical course, samples displayed increasing drug resistance ex vivo with disease progression. Even sensitivity to the monoclonal antibody daratumumab could be measured with the testing methods of this disclosure. The ex vivo drug sensitivities of myeloma cells were found to be consistent with clinical outcomes. Additionally, these tests demonstrated that patients treated with regimens containing one or no drugs that were active ex vivo had significantly poorer prognosis.

This disclosure provides methods for assessing the sensitivity of multiple myeloma cells obtained from a subject to one or more chemotherapeutic agents in an ex vivo assay by contacting the multiple myeloma cells obtained from the subject ex vivo with at least one chemotherapeutic agent. The multiple myeloma cells are incubated with the at least one chemotherapeutic agent to form incubated cells. At least one cell surface protein selected from the group of CD138, CD38, CD45, and CD19, is labeled to form labeled multiple myeloma cells. These labeled multiple myeloma cells are analyzed by flow cytometry to determine the sensitivity and resistance of the subject's multiple myeloma cells to the at least one chemotherapeutic agent.

In these methods, the multiple myeloma cells obtained from the subject may be cellular components of a bone marrow aspirate or peripheral blood from the subject.

In these methods, the at least one chemotherapeutic agent may include a drug known to treat multiple myeloma in a subject. For example, the at least one chemotherapeutic agent may be an alkylating agent, an antimetabolite, a natural product, a hormone, a biologic, an antibody, a proteasome inhibitor, an immunomodulatory imide drug, a platinum coordination complex, or a histone deacetylase inhibitor. Specific chemotherapeutic agents for use in these methods may include one or more of bortezomib, carfilzomib, lenalidomide, pomalidomide, dexamethasone, cyclophosphamide, 4-hydroperoxy cyclophosphamide and daratumumab.

In these methods, the incubation of the cells with the chemotherapeutic agent(s) may continue for a period of time between two hours and 168 hours, for example the incubation may continue for a period of time between 24 hours and 72 hours. Preferably, the incubation continues for a period of about 48 hours.

The incubation of the cells with the chemotherapeutic agent(s) may comprise incubating about $1\times10^2$ to $1\times10^8$ mononuclear cells from the subject with the agent(s). For example, the incubation may include incubating about $1\times10^4$ to $1\times10^5$ mononuclear cells from the subject with the agent(s). Before or during the incubation of the multiple myeloma cells, the cells may be incubated with interleukin-6 (IL-6).

In these methods, the labeling may include contacting the incubated cells with at least one antibody selected from the group of: anti-CD19, anti-CD45, anti-CD38, and anti-CD138 antibodies.

In these methods, the analysis may include contacting the labeled multiple myeloma cells with a fluorescent dye that binds to free amines within the multiple myeloma cells and on the surface of the multiple myeloma cells resulting in less intense fluorescence from live multiple myeloma cells, thereby allowing the detection of a distinction between live and dead cells.

In these methods, the flow cytometry analysis may include gating the multiple myeloma cells on expression of one or more of CD38, CD138, CD19, and CD45. For example, the multiple myeloma cells may be gated on CD19− CD45+/−CD38+ CD138+ and may optionally be verified by expression of clonal light chain restricted to either lambda or kappa.

In these methods, the analysis may determine that the multiple myeloma cells from the subject are sensitive to the at least one chemotherapeutic agent when at least 20% of the incubated multiple myeloma cells are detected to have died relative to the untreated condition. Alternatively or additionally, the analysis may determine that the multiple myeloma cells from the subject are resistant to the at least one chemotherapeutic agent when less than 20% of the incubated multiple myeloma cells are detected to have died relative to the untreated condition.

In these methods, the multiple myeloma cells are obtained from a subject at the time of initial diagnosis with multiple myeloma, and/or at the time of first relapse of multiple myeloma, and/or at the time of second or subsequent relapse of multiple myeloma.

Based on the results of these analysis methods, the multiple myeloma in the subject may be treated with at least one chemotherapeutic agent that was shown to which the subject's treated MM cells are identified to be sensitive to the agent(s).

This Summary is neither intended, nor should it be construed, as being representative of the full extent and scope of the present disclosure. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and the Description of Embodiments and no limitation as to the scope of the present disclosure is intended by either the inclusion or non-inclusion of elements, components, etc. in this Summary. Additional aspects of the present disclosure will become more readily apparent from the Description of Embodiments, particularly when taken together with the drawings.

BRIEF DESCRIPTION OF FIGURES

FIG. 1A shows the MM cell viability after 48 hours from 4 samples thawed and separated into fractions and cultured unselected, or after CD138-selection (normalized to time zero). FIG. 1B shows the ex vivo supplementation of IL6 increased the MM cell populations for 3/5 samples tested (data represent mean±SD). Two-tailed Student's t test, p<0.01. FIG. 1C shows the viability of MM cells decays ex vivo in the first 24 hours, then plateaus at 48 hours (dotted line) (n=3). FIGS. 1D-1E show first, viable MNCs gated based on live/dead staining, followed by subgating sequentially for CD19/CD45, then CD38/CD138, then the monoclonal myeloma population is verified to have high CD46 or CD319 expression.

FIG. 2A shows the drug sensitivity results for "non-plasma cells" (NPCs) from patient samples that are negative for CD138 and CD38 showing little nonspecific effect of anti-myeloma drugs (except cyclophosphamide) on normal cells in ex vivo cultures. Results from three representative assays shown. FIG. 2B shows normal donor bone marrow aspirates profiled for ex vivo drug sensitivity of nonmalignant plasma cells, showing lack of sensitivity to anti-myeloma agents in all three samples tested. FIG. 2C shows samples tested for anti-myeloma effect of 0.1% DMSO, the concentration tested in IMiD treated wells, had no effect in three representative samples.

FIGS. 3A-3H show ex vivo drug sensitivity screens of multiple myeloma patient primary samples from diagnosis through multiple relapses. FIG. 3A shows a heat map of single agent ex vivo drug testing in samples from MM patients at single concentrations (PIs at 2.5 nM, IMiDs at 10 μM, Dex at 1 μM and Cy at 3.75 μM). Samples with <80% of myeloma cells remaining after 48 hr treatment were scored sensitive to the drug (green), >80% resistant (red). FIG. 3B shows that at diagnosis, 83% samples were intrinsically resistant to at least 1 of the 6 anti-myeloma agents tested. FIG. 3C shows that resistance to PIs bortezomib and carfilzomib correlated to lines of prior therapy. FIG. 3D shows that the resistance to IMiDs lenalidomide and pomalidomide also correlated to lines of therapy. FIGS. 3E and 3F show that cyclophosphamide and dexamethasone sensitivity did not correlate with lines of prior therapy. FIGS. 3G and 3H show that the ex vivo results among PI and IMiD classes were highly correlated from sensitive to both (lower left) to resistant to both (upper right). However, differential results favoring one agent in each class (upper left and lower right) were observed. Dashed lines represent 95% confidence intervals. Bor—bortezomib, Car—carfilzomib, Cy—4-hyroxycyclophosphamide, Dex—dexamethasone, Len—lenalidomide, LOT—number of prior lines of therapy, Norm—normalized, PIs—proteasome inhibitors, Pom—pomalidomide.

FIG. 4A shows ex vivo response rates for each drug across the treatment naïve, first relapse, and multi-relapse groups. FIG. 4B shows the number of drugs scored as resistant ex vivo correlated with the number of prior lines of therapy. Data represent mean±SD. Significance calculated by two-way ANOVA, *p<0.05, p<0.01, *p<0.001, ****p<0.0001.

FIGS. 5A and 5B show patients 134 and 576 were tested for ex vivo drug sensitivity both at diagnosis and first relapse, each showing development of decreased sensitivity to agents at relapse. FIG. 5C shows patient 700 had significantly increased drug resistance to lenalidomide, but had increased sensitivity to cyclophosphamide. FIG. 5D shows that patient 614 had significantly increased drug resistance to carfilzomib and lenalidomide with progression of disease. FIG. 5E shows that patient 634 displayed gradually increasing PI resistance across multiple relapse time points and remained IMiD and cyclophosphamide resistant, but notably regained sensitivity to dexamethasone. FIG. 5F shows that patient 646 lost isolated bortezomib sensitivity over time, but also displayed surprising re-sensitization to cyclophosphamide. FIG. 5G shows patient 649 with serial biopsy ex vivo drug sensitivity results, showing no significant changes in drug sensitivity from 1st to 3rd relapses. Data represent mean±SD. Significance calculated by two-way ANOVA, p<0.01, *p<0.001, ****p<0.0001. Bor—bortezomib, Car—carfilzomib, Cy—4-Hydroxy cyclophosphamide, Dex—dexamethasone, norm—normalized, Len—lenalidomide, Pom—pomalidomide, untd—untreated controls FIG. 6A shows that primary MM cells exhibit a dose dependent reduction in viable MM cells after 48 hours ex vivo culture in the presence of daratumumab. FIG. 6B shows that in samples recently exposed to Dara clinically, the flow-cytometry antibody for CD38 was masked by the drug (left panel). This problem was addressed by using a polyclonal antibody for CD38 to unmask CD38 bound to daratumumab (right panel). FIG. 6C shows a Waterfall plot of ex vivo response to 20 nM Dara among newly diagnosed samples is similar to relapsed, daratumumab naïve patients, but daratumumab exposed patients showed much less response. FIG. 6D shows that the ex vivo sensitivity in Dara-naïve samples was significantly better than samples from patients with prior exposure. FIG. 6E shows ex vivo sensitivity to Dara increased with prior therapy, with P value suggestive of significance with additional samples.

FIG. 7A shows that, consistent with unique mechanism of action, Dara activity in patient samples showed no correlation with any of the other anti-myeloma agents tested. FIG. 7B shows that the CD38 expression was significantly higher on MM cells from samples scored as Dara sensitive than those that were resistant. FIG. 7C shows that the ex vivo reduction of primary MM cells exposed to Dara correlated with the level of CD38 expression by flow cytometry. FIG. 7D shows that the ex vivo daratumumab reduction in primary MM cells was largely reversed by macrophage deactivation with clodronate containing liposomes (CL). FIG. 7E shows that Daratumumab did not affect the viability of non-plasma cells in patient samples. FIG. 7F shows that daratumumab did not substantially reduce viability of bone marrow plasma cells from normal donors. Data represent mean+/−SD. Dara—daratumumab, MFI—median fluorescence intensity, NPC—nonplasma cells.

FIG. 8A depicts prior treatment regimens administered to patients grouped by line of therapy. FIG. 8B depicts the pen-transplant history for patients grouped by setting. FIG. 8C shows the ex vivo PI sensitivity in myeloma drug sensitivity testing (My-DST) was significantly lower in bone marrow samples from patients who were relapsed or refractory (Rel/Ref) to prior PI treatment. FIG. 8D shows that the IMiD sensitivity was also significantly lower in bone marrow samples from Rel/Ref patients with history of IMiD treatment. FIG. 8E shows there was no difference observed in cyclophosphamide sensitivity between samples from patients with prior clinical Cy exposure vs those that were Cy naïve. FIG. 8F shows the dexamethasone sensitivity was also not different in samples from treatment naïve patients compared to those with prior Dex treatment. Data points represent the means from each individual sample. Comparisons were made by Mann-Whitney U test (FIG. 8C) or two tailed Student's t test (FIGS. 8D-F). Norm—normalized, Pt—patient. *p<0.05, ***p<0.001.

FIG. 9A shows that the proportional combination effect ("MyDST Comb" from Table 1) vs. depth of clinical response after 4 cycles† of treatment. True positives were defined if the combined EV effect was <50% and clinical response was at least PR (50% decrease). True negatives were defined if the combined EV effect was >50% and PR was not achieved. FIG. 9B is a plot showing the depth of clinical response in newly diagnosed patients relative to the goals of VGPR (90% decrease) and CR (dotted lines) after receiving 4 cycles† induction treatment categorized by the number of EV sensitive drugs in My-DST. ex vivo FIG. 9C is a plot showing the depth of clinical response in relapsed patients relative to the clinical goals of PR and CR (dotted lines) after receiving 4 cycles treatment in the next LOT categorized by the number of EV sensitive drugs in My-DST. FIG. 9D shows a newly diagnosed patient #847 was a frail patient started on initial 2-drug therapy. Ex vivo Testing showed PI sensitivity and IMiD resistance (data represent mean+/−SD). FIG. 9E shows that the clinical response of patient #847 showed MR from lenalidomide and dexamethasone, but CR after being switched to bortezomib and dexamethasone.

DETAILED DESCRIPTION

Figure 1A:
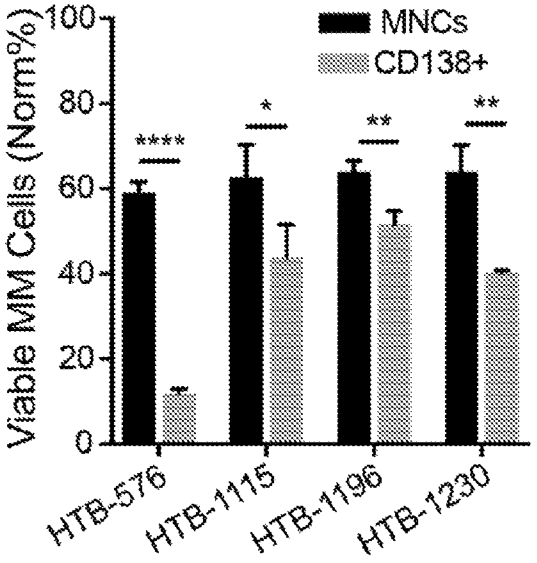
FIGS. 1A-1E show the development of flow cytometry-based measurement of drug sensitivity in primary myeloma patient samples ex vivo.

This disclosure provides methods of determining the sensitivity of multiple myeloma cells from a subject to available chemotherapeutic agents.

Multiple myeloma (MM) is a B cell malignancy characterized by the accumulation of plasma cells in the bone marrow (BM) and the secretion of large amounts of monoclonal antibodies that ultimately causes bone lesions, hypercalcemia, renal disease, anemia, and immunodeficiency. MM is characterized by monoclonal proliferation of malignant plasma cells (PCs) in the BM, the presence of high levels of monoclonal antibody in the serum, the development of osteolytic bone lesions, and the induction of angiogenesis, neutropenia, amyloidosis, and hypercalcemia. MM is seen as a multistep transformation process. Although little is known about the immortalizing and initial transforming events, the initial event is thought to be the immortalization of a plasma cell to form a clone, which may be quiescent, non-accumulating and not cause end-organ damage due to accumulation of plasma cells within the bone marrow (MGUS). Smoldering MM (SMM) also has no detectable end-organ damage, but differs from MGUS by having a serum level higher than 3 g/dl or a BM PC content of more than 10% and an average rate of progression to symptomatic MM of 10% per year. An abnormal immunophenotype distinguishes healthy plasma cells (PCs) from tumor cells. Healthy BM PCs are CD38+CD138+CD19+CD45+CD56−. Although MM tumor cells also are CD38+CD138+, 90% are CD19−, 99% are CD45− or CD45 lo, and 70% are CD56+.

The prognosis and treatment of this disease has greatly evolved over the past decade due to the incorporation of new agents that act as immunomodulators and proteosome inhibitors. Despite recent progress with new drug treatments, patients only experience somewhat longer periods of remission. Because of the development of drug resistance and relapse, MM remains an incurable disease.

Because MM is a disease characterized by multiple relapses, the order/sequencing of the different effective treatment options is crucial to the outcome of MM patients. In the frontline setting, the first remission is likely to be the period during which patients will enjoy the best quality of life. Thus, one goal is to achieve a first remission that is the longest possible by using the most effective treatment upfront. At relapse, the challenge is to select the optimal treatment for each patient while balancing efficacy and toxicity. The decision will depend on both disease- and patient-related factors. The drug sensitivity testing methods of this disclosure provides the capability of testing the efficacy of a potential chemotherapeutic therapy, prior to patient treatment, and can therefore have a major impact in the management of this disease.

Thus, the present disclosure provides methods for assessing sensitivity of human multiple myeloma cells obtained from a subject to chemotherapeutic agents in an ex vivo microenvironment by incubating multiple myeloma (MM) cells obtained from a subject ex vivo with at least one chemotherapeutic agent; labeling at least one protein selected from the group consisting of CD138, CD38, CD45, CD19 on the surface of the incubated cells to form labeled MM cells; and analyzing the labeled MM cells by high-throughput flow cytometry to determine the sensitivity and resistance of the labeled MM cells treated to the chemotherapeutic agent.

In these methods, the myeloma cells obtained from the subject may be cellular components of either bone marrow aspirate or peripheral blood. For example, the myeloma cells may be cellular components of bone marrow aspirate, and/or components of peripheral blood from the subject, and/or cellular components of plasma autologous to the patient.

The chemotherapeutic agents used in these methods may be any chemical substance that can treat disease, and specifically includes antineoplastic drugs used alone or in combination as a cytotoxic standardized regimen to treat multiple myeloma. The chemotherapeutic agents may be divided into several categories including, but not limited to, immunomodulatory drugs, proteasome inhibitors, alkylating agents, antimetabolites, natural products, hormones and related agents, biologics, and antibodies. Thus, the chemotherapeutic agent(s) used in these methods may be any drug known to treat MM in a subject. In particular, the chemotherapeutic agent(s) used in these methods may be selected from the group consisting of an alkylating agent, an antimetabolite, a natural product, a hormone, a biologic, an antibody, a proteasome inhibitor, an immunomodulatory drug, a platinum coordination complex, and a histone deacetylase inhibitor. Specific chemotherapeutic agents may include one or more chemotherapeutic agents selected from the group consisting of bortezomib (Bor), carfilzomib (Car), lenalidomide (Len), pomalidomide (Pom), dexamethasone, cyclophosphamide (Cy), 4-hydroperoxy cyclophosphamide (4-HC) and daratumumab.

The methods of this disclosure may be optimized for efficiency and accuracy by, for example, optimizing the period of time during which the MM cells are incubated with the chemotherapeutic agent, or the number of MM cells obtained and incubated. For example, in the methods of this disclosure, the cells may be incubated with the chemotherapeutic agent for a period of time between 2 hours and 168 hours. More optimal incubation times may include a period of time between 24 hours and 72 hours, or a period of about 48 hours.

Similarly, in the methods of this disclosure, the cells obtained from a subject may include about $1\times10^2$ to $1\times10^8$ mononuclear cells form the subject. Optimally, the incubated cells may include about $1\times10^4$ to $2\times10^5$ mononuclear cells form the subject.

Additionally, certain chemical agents, such as growth factors, cytokines, etc. may be included in the incubation of the MM cells from the subject to enhance any one of the growth, survival, or maintenance of the ex vivo culture. For example, the cells may be incubated with interleukin-6 (IL-6) during all or part of the incubation as a further optimization of the testing methods of this disclosure.

Additionally, the culture media may mimic conditions in human plasma. For example, the amino acids and other nutrients may be added individually to concentrations similar to human plasma concentrations of those elements.

Cytometry is a process in which physical and/or chemical characteristics of single cells, or by extension, of other biological or nonbiological particles in roughly the same size or stage, are measured. In flow cytometry, the measurements are made as the cells or particles pass through a measuring apparatus (a flow cytometer) in a fluid stream.

A differential label is generally a stain, dye, marker, antibody or antibody-dye combination, or intrinsically fluorescent cell-associated molecule, used to characterize or contrast components, small molecules, macromolecules, e.g., proteins, and other structures of a single cell or organism. The term "dye" (also referred to as "fluorochrome" or "fluorophore") as used herein refers to a component of a molecule that causes the molecule to be fluorescent. The component is a functional group in the molecule that absorbs energy of a specific wavelength and re-emits energy at a different (but equally specific) wavelength. The amount and wavelength of the emitted energy depend on both the dye and the chemical environment of the dye. Many dyes are known, including, but not limited to, FITC, R-phycoerythrin (PE), PE-Texas Red Tandem, PE-Cy5 Tandem, propidium iodide, EGFP, EYGP, ECF, DsRed, allophycocyanin (APC), PerCp, SYTOX Green, courmarin, Alexa Fluors (350, 430, 488, 532, 546, 555, 568, 594, 633, 647, 660, 680, 700, 750), Cy2, Cy3, Cy3.5, Cy5, Cy5.5, Cy7, Hoechst 33342, DAPI, Hoechst 33258, SYTOX Blue, chromomycin A3, mithramycin, YOYO-1, SYTOX Orange, ethidium bromide, 7-AAD, acridine orange, TOTO-1, TO-PRO-1, thiazole orange, TOTO-3, TO-PRO-3, thiazole orange, propidium iodide (PI), LDS 751, Indo-1, Fluo-3, DCFH, DHR, SNARF, Y66F, Y66H, EBFP, GFPuv, ECFP, GFP, AmCyanl, Y77W, S65A, S65C, S65L, S65T, ZsGreen1, ZsYellow1, DsRed2, DsRed monomer, AsRed2, mRFP1, HcRed1, monochlorobimane, calcein, the DyLight Fluors, cyanine, hydroxycoumarin, aminocoumarin, methoxycoumarin, Cascade Blue, Lucifer Yellow, NBD, PE-Cy5 conjugates, PE-Cy7 conjugates, APC-Cy7 conjugates, Red 613, fluorescein, FluorX, BODIDY-FL, TRITC, XFigure US20160137986A1-20160519-P00001rhodamine, Lissamine Rhodamine B, Texas Red, TruRed, and derivatives thereof.

Flow cytometry is a technique for counting, examining, and sorting microscopic particles suspended in a stream of fluid. It allows simultaneous multi-parametric analysis of the physical and/or chemical characteristics of single cells flowing through an optical and/or electronic detection apparatus.

Flow cytometry utilizes a beam of light (usually laser light) of a single wavelength that is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals found in the particle or attached to the particle may be excited into emitting light at a lower frequency than the light source. This combination of scattered and fluorescent light is picked up by the detectors, and by analyzing fluctuations in brightness at each detector (usually one for each fluorescent emission peak) it then is possible to derive various types of information about the physical and chemical structure of each individual particle. FSC correlates with the cell volume and SSC depends on the inner complexity of the particle (i.e. shape of the nucleus, the amount and type of cytoplasmic granules or the membrane roughness).

Fluorescence-activated cell sorting (FACS) is a method for sorting a heterogeneous mixture of biological cells into one or more containers, one cell at a time, based upon the specific light scattering and fluorescent characteristics of each cell. FACS is a specialized type of flow cytometry. It provides a method for sorting a heterogeneous mixture of biological cells into two or more containers, one cell at a time, based upon the specific light scattering and fluorescent characteristics of each cell. It provides fast, objective and quantitative recording of fluorescent signals from individual cells as well as physical separation of cells of particular interest. Utilizing FACS, a cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell being in a droplet. Before the stream breaks into droplets the flow passes through a fluorescence measuring station where the fluorescent character of interest of each cell is measured. An electrical charging ring or plane is placed just at the point where the stream breaks into droplets. A charge is placed on the ring based on the prior light scatter and fluorescence intensity measurements, and the opposite charge is trapped on the droplet as it breaks from the stream. The charged droplets then fall through an electrostatic deflection system that diverts droplets into containers based upon their charge. In some systems the charge is applied directly to the stream while a nearby plane or ring is held at ground potential and the droplet breaking off retains charge of the same sign as the stream. The stream is then returned to neutral after the droplet breaks off.

Cell surface "cluster of differentiation" (CD) antigen molecules preferentially expressed by B cells include CD38, CD138, CD19, and CD45. Thus, the MM cells in incubation may be selectively labeled for analysis by flow cytometry by labeling or "tagging" the cells with one or more antibodies that specifically bind to CD antigens associated with B cells. This may include at least one antibody selected from the group consisting of: anti-CD19, anti-CD45, anti-CD38, anti-CD138, anti-CD319, or anti-CD46 antibodies. Thus, the flow cytometry analysis of the incubated and labelled MM cells may include gating the MM cells on expression of CD38, CD138, CD19, and CD45.

Additionally, in order to effectively and quickly differentiate between live and dead MM cells amongst the incubated cells, a dye or tag or label that differentially binds to live versus dead cells may be utilized in the methods of this disclosure. For example, the incubated MM cells may be contacted with a fluorescent dye that binds to free amines within the MM cells and on the surface of the MM cells resulting in less intense fluorescence from live MM cells.

The analysis of the number of live and dead cells amongst the incubated cells can inform the determination of the sensitivity of the labeled MM cells to the chemotherapeutic agent. A cut off number of live or dead cells may be selected for expediency and/or consistency. For example, sensitivity of the subject's MM cells to the chemotherapeutic agent(s) may be determined in the methods of this disclosure as detecting loss of viability of at least 20% of the incubated MM cells. In a related example, determining resistance of the subject's MM cells to the chemotherapeutic agent(s) may be determined in the methods of this disclosure as detecting loss of viability of less than 20% of the incubated MM cells.

A useful immunophenotypic determinant of MM is light chain restriction. A MM clone expresses a uniform quantity of surface Ig, while polyclonal B-cell have a heterogenous surface Ig expression. This results in a narrower distribution of staining intensity with anti-light chain reagents in the monoclonal MM cells compared to the polyclonal B-cells. Normal and reactive B-cell populations typically exhibit kappa and lambda light chain expression at an expected ratio, while neoplastic cells (MM cells) exhibit overexpression of either kappa or lambda light chain. In some embodiments, clonality of the MM cells from a patient is confirmed by determination of kappa and/or lambda light chain restriction. This can be achieved by specifically staining kappa and lambda light chains.

In some embodiments, cells are analyzed by flow cytometry to determine the sensitivity and resistance of a subject's MM cell to a chemotherapeutic agent. The cells can be dyed, tagged, or labeled with a dye or tag or label that differentially binds to live versus dead cells; tagged with at least one antibody selected from the group of anti-CD19, anti-CD45, anti-CD38, anti-CD138, anti-CD319, and anti-CD46 antibody; specifically staining kappa and lambda light chains; or a combination thereof. A hierarchical or Boolean gating strategy can then be employed to identify those MM cells of the patient that are sensitive or resistant to the chemotherapeutic agent(s) based on whether a cell is alive, it's CD profile, and/or it's clonality.

In the methods of this disclosure, the MM cells may be obtained from the subject at different times during the course of the subject's disease, thereby permitting evaluation or monitoring of the subject's disease progression. For example, the methods of this disclosure may be conducted using MM cells obtained from the subject at the time of initial diagnosis with MM, and/or at the time of first relapse of MM in the subject, and/or at the time of second or subsequent relapse of MM in the subject.

The methods of this disclosure provide a clinically useful temporal evaluation of the MM cells in a subject, which information can be used to guide chemotherapeutic treatment of MM in the subject. Thus, the methods of this disclosure may include initiating or modifying a chemotherapeutic therapy to treat MM in the subject with at least one chemotherapeutic agent, for example, to which the subject's MM cells are identified to be sensitive in comparison to untreated control cells.

Treating the subject with the identified chemotherapeutic agent(s) may include abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Thus, the term "treat" as used in this disclosure refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously symptomatic for the disorder(s).

Another aspect of this disclosure provides kits for testing a subject diagnosed with MM to evaluate sensitivity and/or resistance to a chemotherapeutic agent. The kit may include at least one cell surface marker, such as an anti-CD19, an anti-CD45, an anti-CD38, an anti-CD38, an anti-CD138, an anti-CD319, and/or anti-CD46 antibody, which antibody may be labeled with a chemical that can be detected in flow cytometric assays. Alternatively or additionally, the kit may also include at least one chemical that differentially interacts with live and dead cells, such as a dye that reacts with free amines on the interior and the surface of cells, resulting in less intense fluorescence for live cells. The kit may additionally include at least stain or antibody for each of kappa and lambda light chains. These kits may also include a container, a package insert or label describing methods of conducting the testing procedures of this disclosure, and items useful for conducting these methods such as sterilized plasticware for obtaining and testing a sample of cells from the subject.

EXAMPLES

The following methods were used when conducting experiments described in Examples 1-4, below:

Patient Sample Processing

Extra bone marrow aspirate was collected from patients at University of Colorado Blood Cancer and Bone Marrow Transplant Program after informed consent. Samples from patients with multiple myeloma or smoldering myeloma were obtained from the hematologic malignancies tissue bank with protocol approval from the Western Institutional Review Board. MNCs were isolated from the samples using SepMate Ficoll-Plaque tubes (StemCell Technologies). Normal donor samples were purchased from AllCells. Selection of $CD138^+$ cells was performed with magnetic bead columns (Miltenyi), only where specifically noted. Samples were cryopreserved in freezing medium consisting of Iscove's Modified Dulbecco's Medium, 45% fetal bovine serum (FBS), and 10% Dimethyl sulfoxide (DMSO) at 10 million cells/mL.

Ex Vivo Drug Sensitivity Testing

De-identified primary myeloma samples were thawed and incubated with 100 μg DNase I (Sigma-Aldrich). Samples were washed twice with 10 mL Dulbecco's Phosphate Buffered Saline (DPBS) without calcium and magnesium. Cells were resuspended in RPMI1640 medium containing L-glutamine with 10% FBS and 100 U/mL penicillin and 100 μg/mL streptomycin (Thermo Fisher Scientific) and 2 ng/mL IL-6 (PeproTech) at 37° C. for 2 hours. Cells were then transferred to 96-well plates at $4.5\times10^5$ cells/mL (90,000 MNCs per well) and drug treated for 48 hours. PIs, IMiDs and Dex were purchased from Thermo Fisher. 4-hydroperoxy cyclophosphamide (4-HC), was purchased from Santa Cruz Biotechnology. Stock drug solutions were prepared at 10 mM in DMSO and stored at −20° C. until use. Dara was obtained from University of Colorado Health Pharmacy. Clodronate-liposomes were purchased from Encapsula Nanosciences to block macrophage activity.

Flow Cytometry

After 48-hour treatment primary samples were washed in 1× cold DPBS and re-suspended in BD Brilliant Stain Buffer (BD Biosciences) in a 96-well v-bottom plate. Cells were treated with FcR Blocking Reagent (Miltenyi Biotec) for 5 minutes and then surface stained with the antibodies anti-CD19-BV786, anti-CD45-BV510, monoclonal anti-CD38-BV421 or multi-epitope anti-CD38-FITC (ALPCO), anti-CD138-BV421 and anti-CD319-APC or anti-CD46 conjugated to Alexa647 with the Antibody Labeling Kit (In Vitrogen). Intracellular staining with anti-kappa-BV605 and anti-lambda-PE light chains was performed after paraformaldehyde fixation and permeabilization. All antibodies were purchased from BD Biosciences, except as noted. After staining, samples were washed with 100 μl DPBS containing 2% FBS (FACS buffer) and re-suspended in 250 μL. Viability staining was done using the LIVE/DEAD Fixable Near-IR Kit (Invitrogen, Carlsbad California). Flow cytometry data was collected using a FACSCelesta (BD) equipped with a high throughput sampler (FITS). For each well a fixed volume of 175 μL was collected by the HTS. Data analysis was completed using FlowJo software.

Statistical Analysis

Figures were generated using Prism 8 (GraphPad) with means and standard deviations (SDs). Two-tailed Student's t-test was used comparing 2 means. Data were analyzed using generalized linear models (ANOVA and mixed effects models)—applying Tukey's correction for multiple comparisons. When normality assumptions were not met, the Mann-Whitney U-test was used. Survival analysis was conducted using SAS version 9.4 (SAS Institute), with follow-up calculated using reverse Kaplan-Meier method and hazard ratios by Cox proportional hazard models. Date of last follow-up was used as a censoring date for living patients. The stratification of patient characteristics by drug sensitivity groups was compared using Fisher's exact test.

Example 1—Development of Myeloma Drug Sensitivity Testing (My-DST)

Figure 1B:
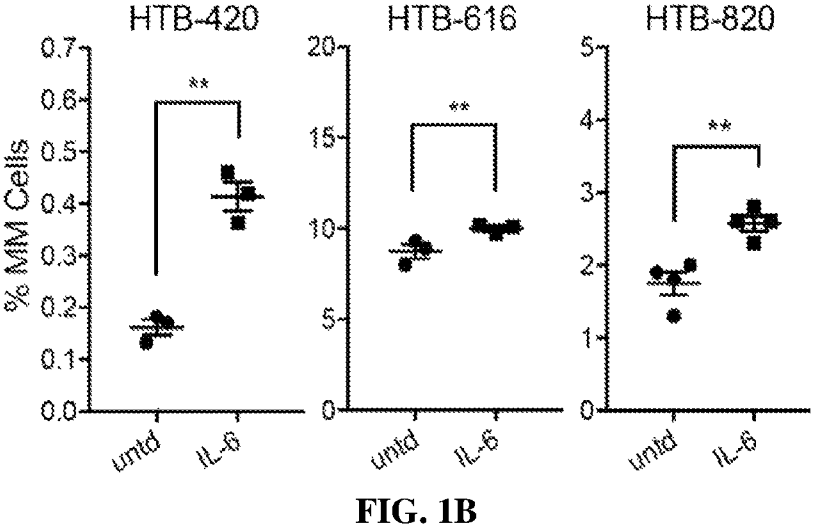
Figure 1C:
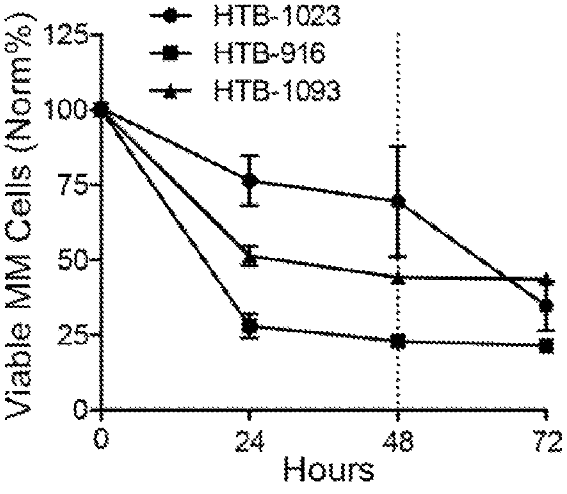

To design an assay to measure ex vivo drug sensitivity of MM cells from primary BM aspirates that could identify drugs with best activity for an individual patient, the first challenge was to measure drug activity in MM primary samples to optimize the baseline viability of the cells ex vivo. Thus, conditions that improve primary MM cell viability ex vivo were first tested. BM MNCs were cultured, rather than CD138-selected MM cells, to avoid mechanical perturbation of the cells and preserve the composition of the BM microenvironment known to influence MM cell viability and drug sensitivity. In multiple samples, MM cell viability was indeed improved in unselected MNC cultures compared to CD138-selected cultures, sometimes drastically (FIG. 1A). IL-6 has been reported to be a key signal for MM cell survival and proliferation. Consistent with this, IL-6 addition attenuated MM cell viability loss in culture for some patient samples (FIG. 1B). To find the optimal time point to measure drug sensitivity in culture, samples were cultured over time and viability monitored. The viability of primary MM cells in the presence of MNCs ex vivo typically drops primarily in the first 24 hours, then stabilizes through 72 hours (FIG. 1C). These findings were used to set the culture conditions to profile MM drug sensitivity.

Figure 1D:
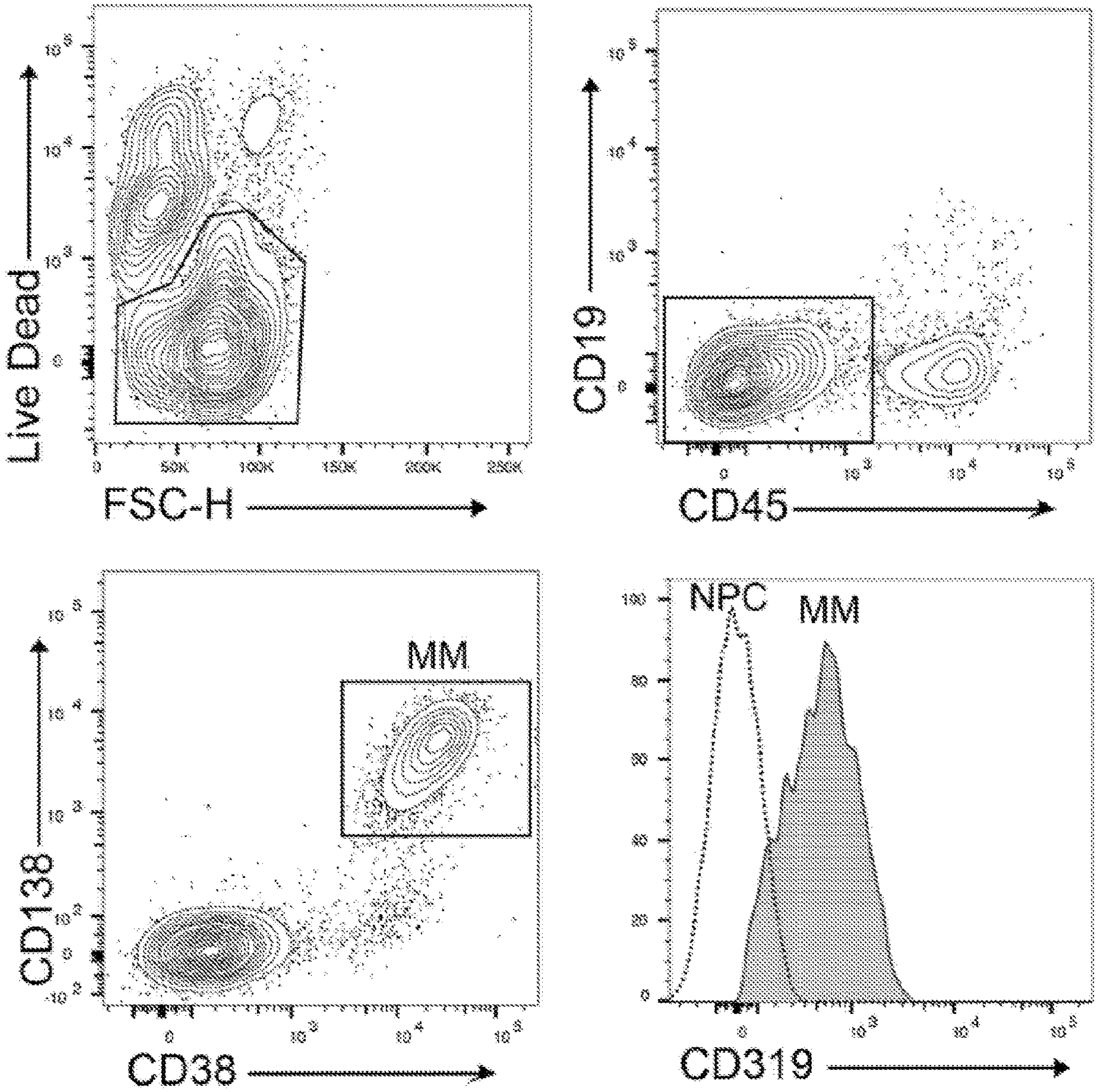
Figure 1E:
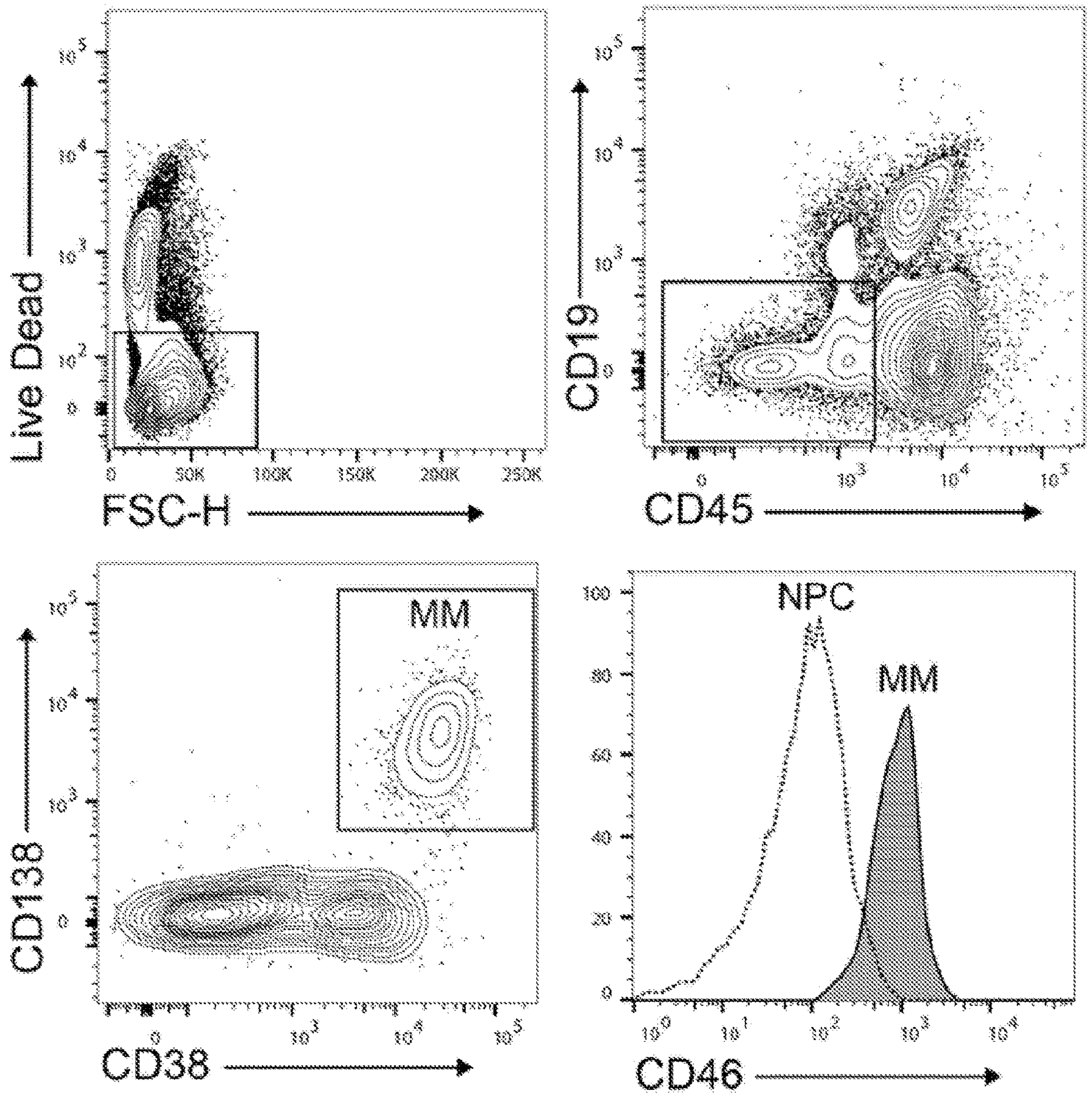
Figure 1F:
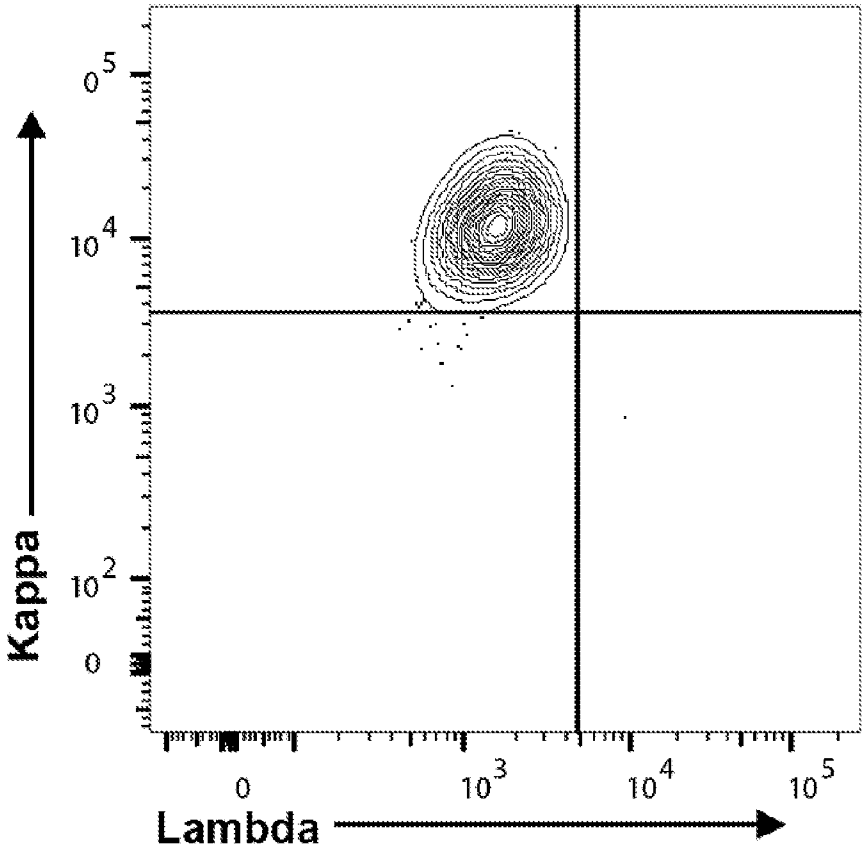
FIG. 1F shows that in parallel intracellular flow cytometry, the gating for MM cells is verified for clonal expression of kappa or lambda matching the patient's clinical information.
Figure 1G:
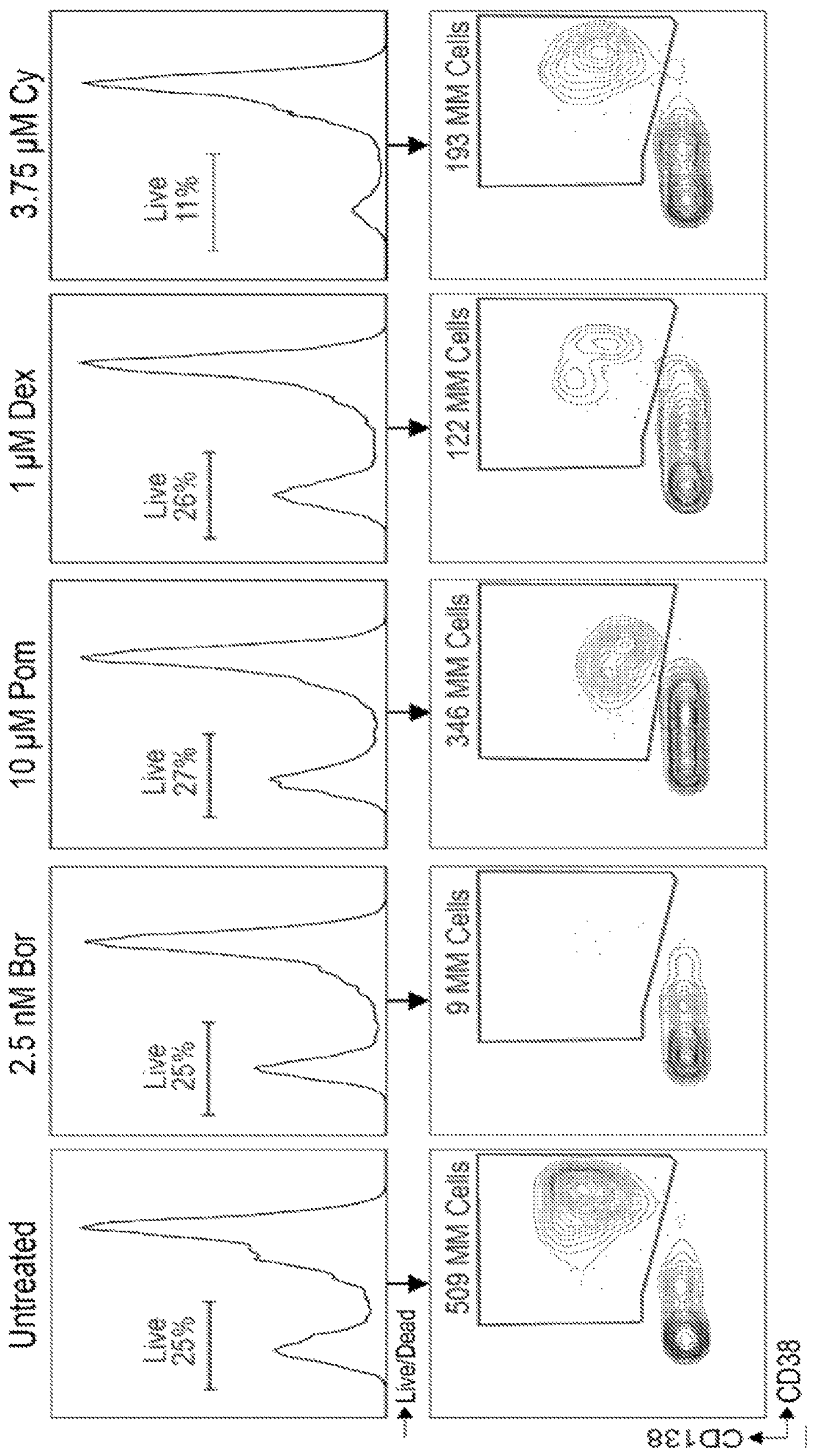
FIG. 1G shows the representative experiment with a MM patient sample treated with anti-myeloma drugs for 48 hours, followed by flow cytometry. Live cells are first gated by live/dead stain, followed by measuring surviving MM cells, which are typically CD45−/CD19−/CD38+/CD138+ (CD19/CD45 gating not shown). Anti-myeloma drug treatment specifically reduces the number of MM cells at 48 hours.

To profile response to the agents commonly used in clinic, patient samples were initially screened with a panel including bortezomib (Bor), carfilzomib (Car), lenalidomide (Len), pomalidomide (Pom), Dex and Cy (tested as its active metabolite "4-HC"). MNCs are cultured for 48 hours, followed by flow cytometry to measure the surviving MM cell population. To accurately measure the MM cells on a sample-by-sample basis, cells were labeled for surface expression of CD138, CD38, CD45, CD19, CD319 and CD46. CD319 and/or CD46 are other markers highly expressed on MM cells, and thus were used to verify the purity of the MM population (FIG. 1D-1E). In parallel, intracellular flow cytometry for kappa and lambda was used to verify the clonality and individualize the MM population gating (FIG. 1F). PIs, IMiDs and Dex each reduced viability specifically in the MM cells, compared to untreated controls (FIG. 1G). In contrast, Cy reduced viable MM cells, but sometimes showed nonspecific cytotoxicity on the bulk MNC population (FIG. 1G, far right panels). Thus, this approach isolates the MM cells in each individual sample, similar to clinical flow cytometry, with the additional output of measuring drug sensitivity.

Figure 1H:
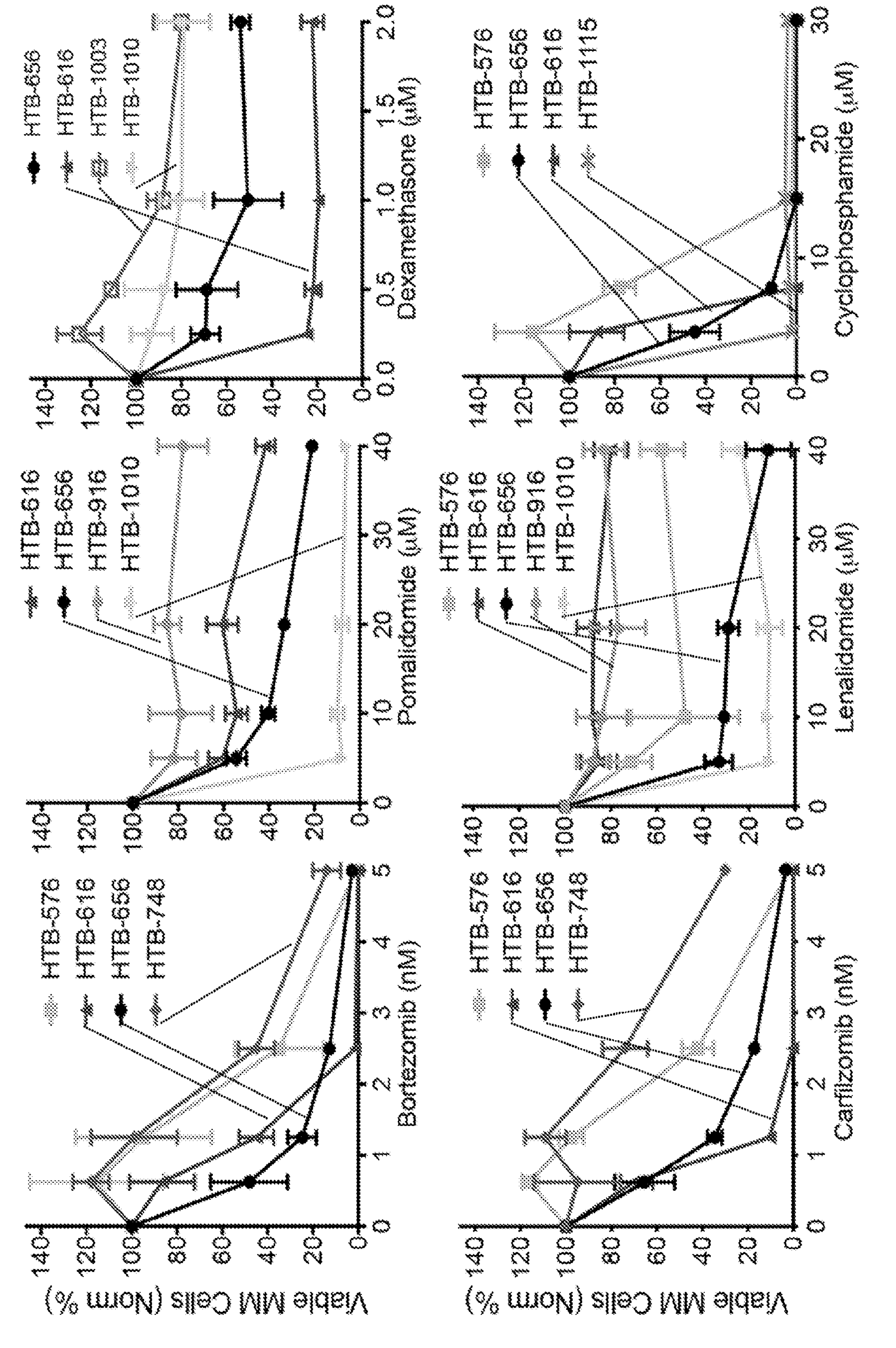
FIG. 1**H shows the dose response for anti-myeloma drugs with this approach to measure drug sensitivity in patient samples. HTB—hematology tissue bank, Norm—normalized.
Figure 2A:
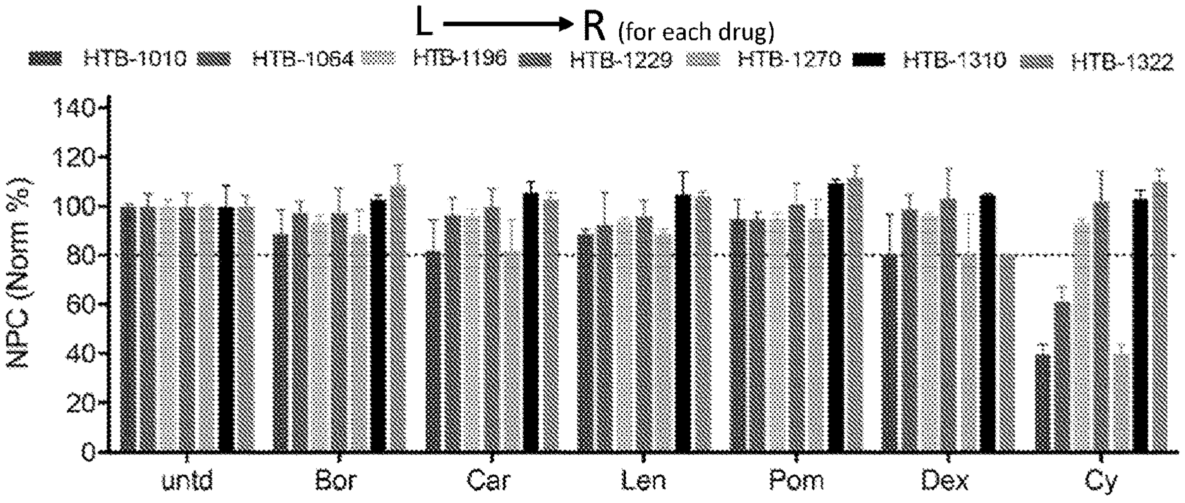
FIGS. 2A-2C show quality control experiments for the optimization of ex vivo myeloma drug sensitivity testing (My-DST) in multiple myeloma primary samples.
Figure 2B:
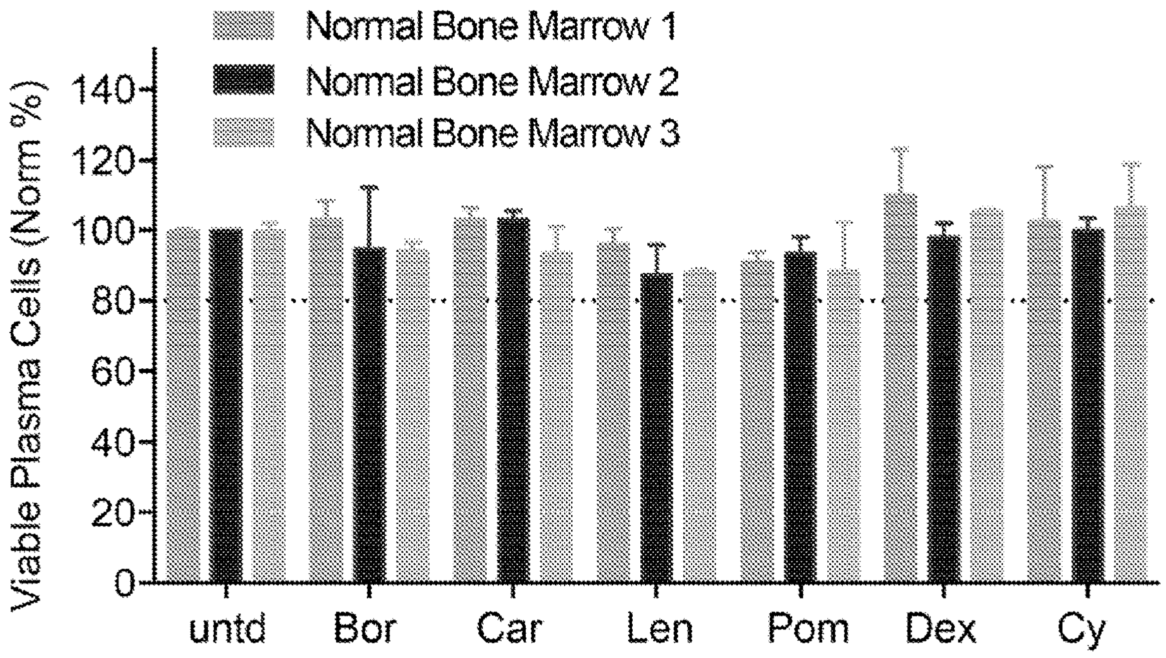
Figure 2C:
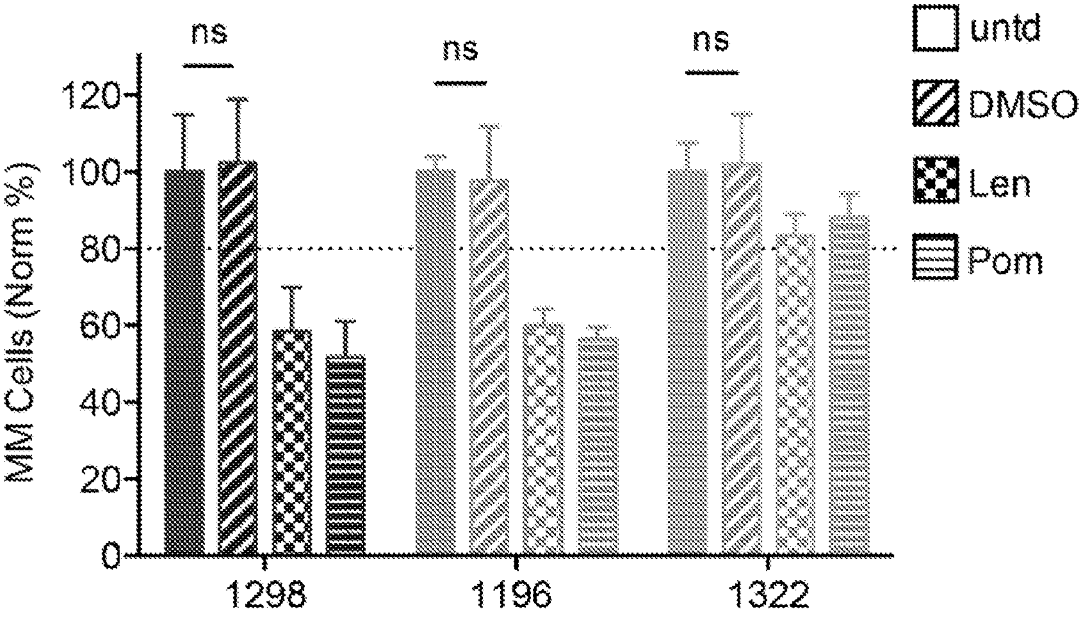

For rapid screening, single concentrations of each drug were sought that produce an expected decrease in MM cell viability by which to judge sensitivity versus resistance. This was started by establishing the dose response to each drug under the above conditions. Each condition was performed in triplicate and normalized compared to untreated control. Newly diagnosed, drug naïve MM patient samples were treated with graded drug concentrations, confirming similar drug potencies in the setting of our assay to published cell line results (FIG. 1H). In contrast, the viability of the nonplasma cells (NPCs), ie the normal MNCs in the cultures, was not affected by anti-myeloma drugs, again with the occasional exception of Cy (FIG. 2A). Interestingly, the viability of plasma cells from BM aspirates from normal donors were not affected by anti-myeloma drugs tested (FIG. 2B). Untreated controls with or without equivalent DMSO to the IMiD treated wells (0.1%) were not significantly different (FIG. 2C). Based on the dose-response relationships for the agents tested, concentrations were selected of 2.5 nM PIs, 10 μM IMiDs, 10 μM Dex and 3.75 μM Cy for rapid throughput testing.

Example 2—Testing in Patient Samples from Diagnosis to Multiple Relapses

Figure 3B:
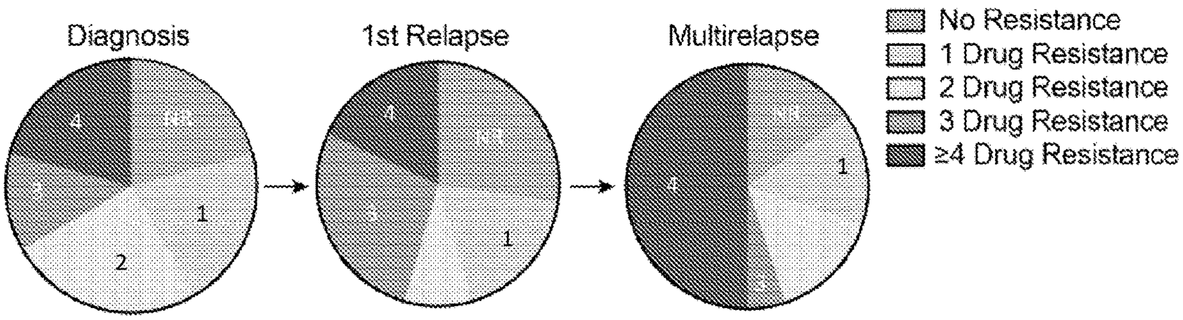
Figure 3C:
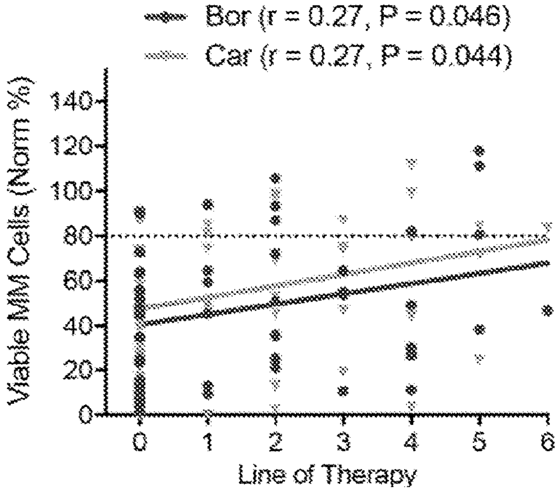
Figure 3D:
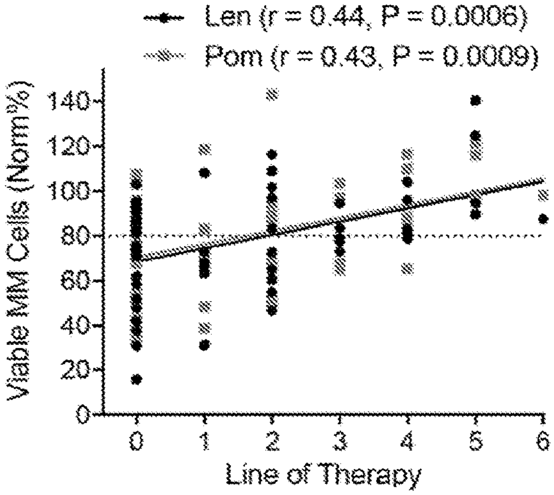
Figure 3E:
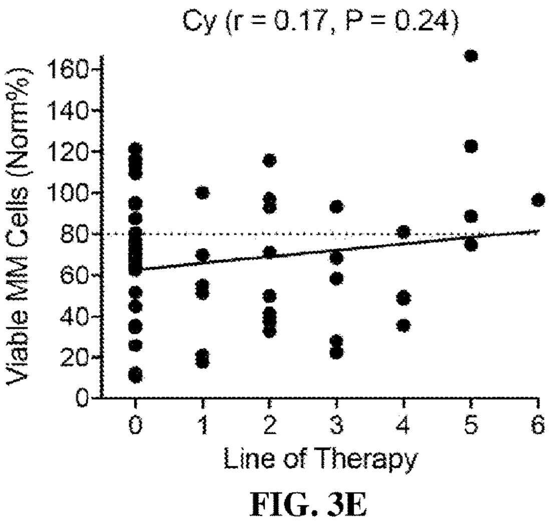
Figure 3F:
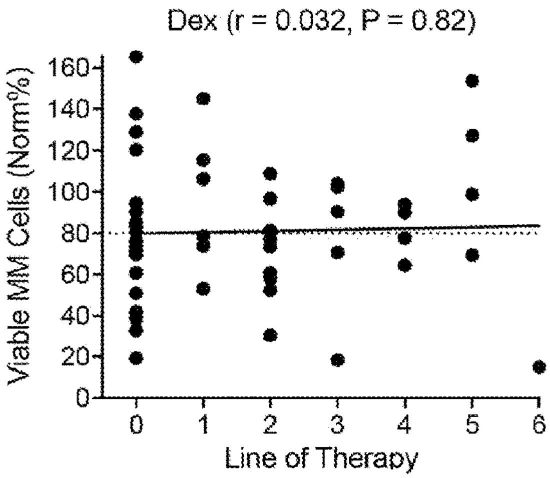
Figure 3G:
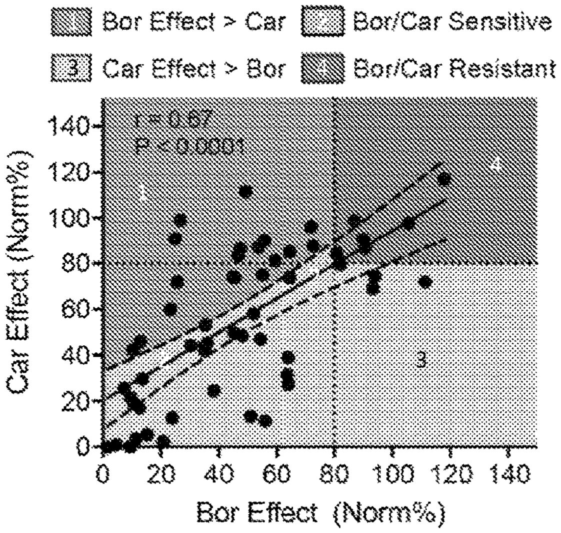
Figure 3H:
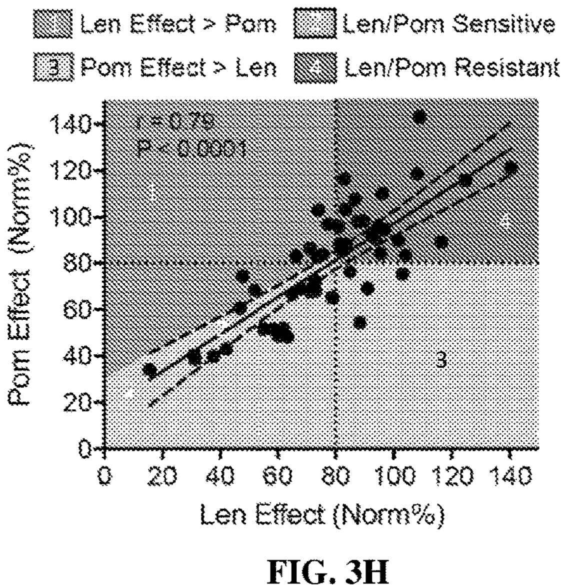

Single concentration drug sensitivity profiling was completed on 55 patient samples from diagnosis (n=24), first relapse (n=12) and after multiple relapses (n=19) (FIG. 3A). To differentiate sensitivity and resistance, 80% MM cell survival (i.e. 20% loss) was used as a cutoff. Mild inherent resistance to varied tested agents was evident at diagnosis and acquired resistance progressively increased with lines of therapy (LOT) until multidrug resistance predominated (FIG. 3B). The testing methods of this disclosure displayed significant correlation for LOT with increasing resistance to Bor (r=0.27, P=0.046), Car (r=0.27, P=0.044), Len (r=0.44, 0.0006) and Pom (r=0.43, P=0.0009) (FIGS. 3C and 3D). However, a significant relationship was not seen for Cy (r=0.17, P=0.24) and Dex (r=0.032, P=0.82) (FIGS. 3E and 3F). The ex vivo sensitivity for Bor and Car were highly correlated (r=0.67, p<0.0001) from sensitive to both, to resistant to both, but occasional differential results favoring Bor or Car were observed (FIG. 3G). The ex vivo results for the tested IMiDs were even more highly correlated (r=0.79, p<0.0001), with fewer samples showing greater sensitivity differentially to Len or Pom (FIG. 3H). Taken in total, screening patient samples from diagnosis to multiple relapses captured differential drug sensitivities in individual patients and recapitulated the progressive development of resistance with disease progression.

Figure 4A:
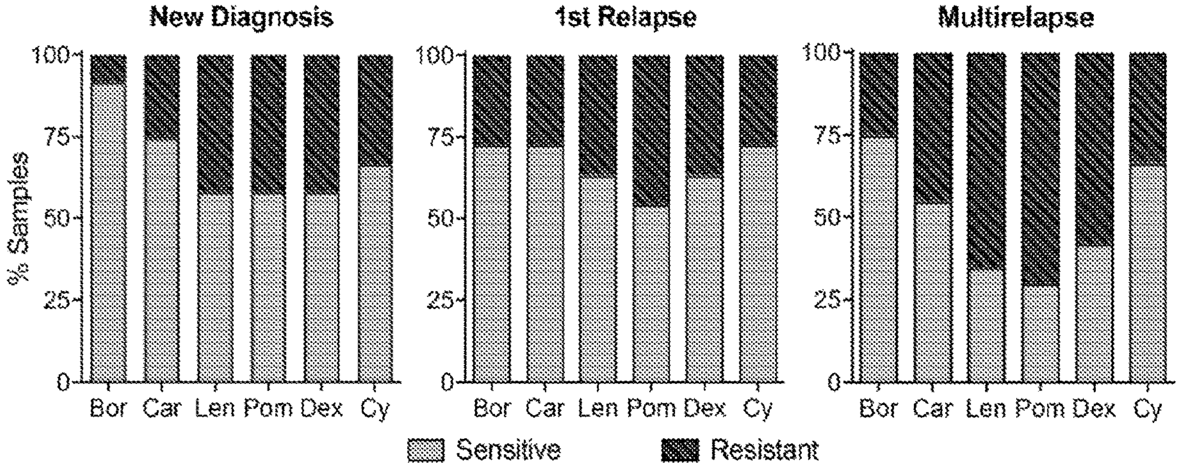
FIGS. 4A-4B show the evolution of drug resistance in patients with multiple myeloma.
Figure 4B:
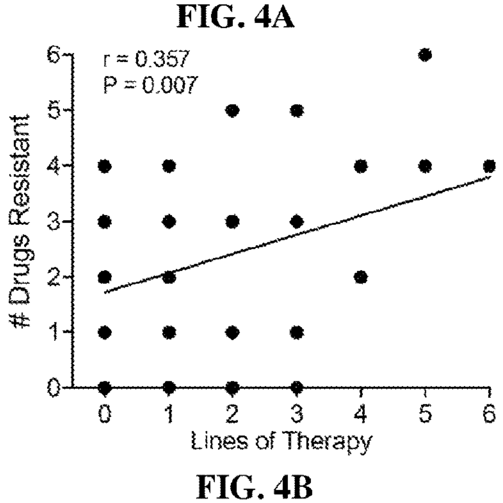
Figure 5A:
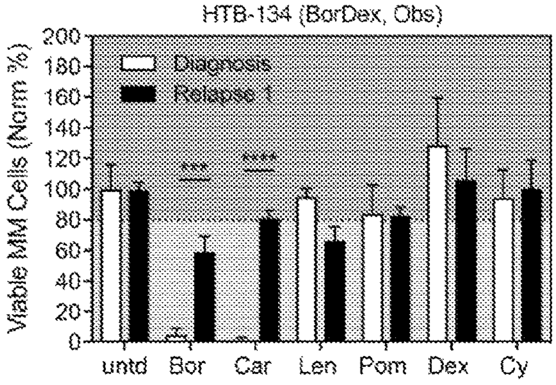
FIGS. 5A-5G show drug sensitivity profile results for myeloma patients with biopsies from multiple time points.
Figure 5B:
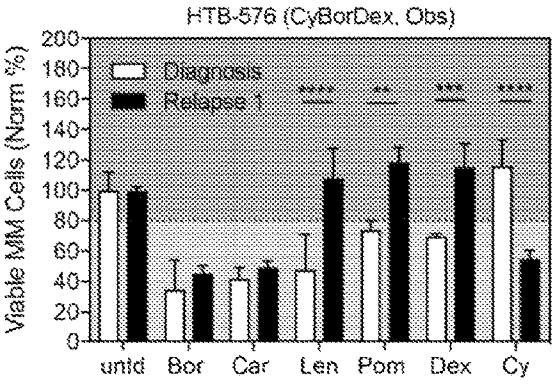
Figure 5C:
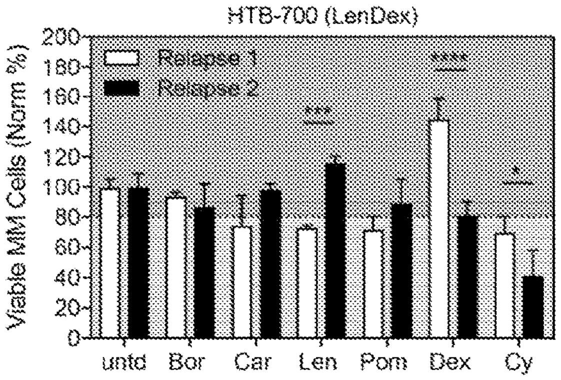
Figure 5D:
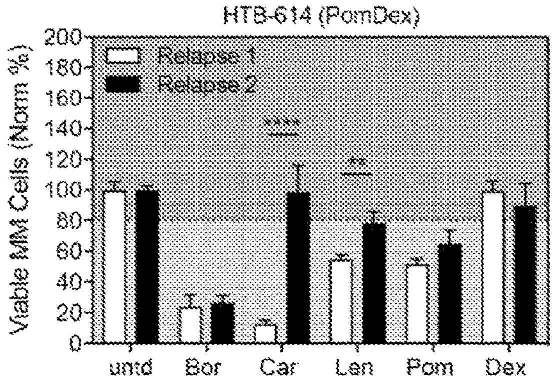
Figure 5E:
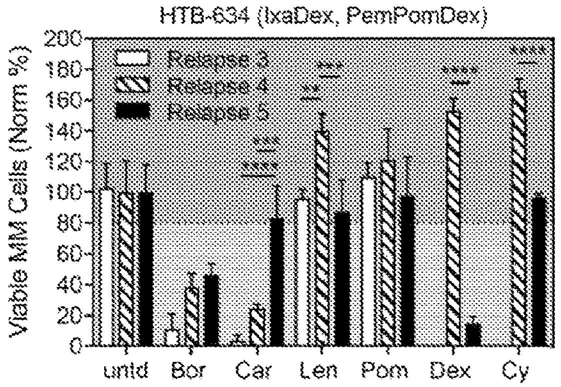
Figure 5F:
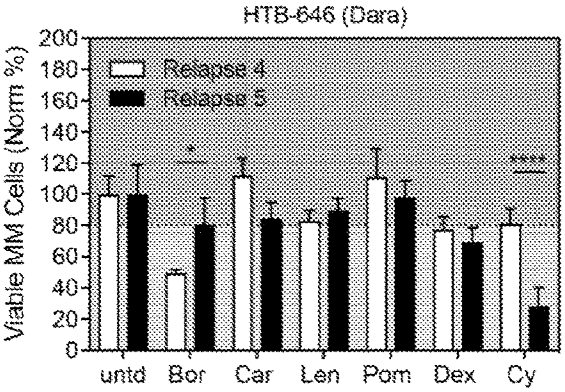
Figure 5G:
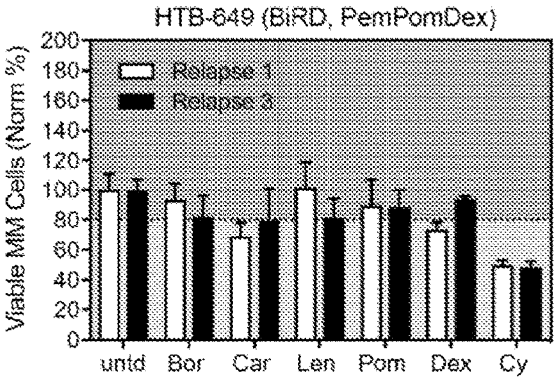

As further evidence that these testing procedures can reliably measure clinically relevant drug activity, the ex vivo response rate patterns and intra-patient evolution of resistance was analyzed. The ex vivo response rates for the key clinically used agents was high at diagnosis, then decreased with progressive relapses (FIG. 4A). The line of therapy correlated significantly with the number of drugs scored as resistant in ex vivo testing (FIG. 4B). Of the patients in this study, 7 were tested at multiple timepoints in their disease course. Looking at the evolution of drug resistance within this subgroup of patients showed trends in the development of drug resistance. Relapsed patients 649, 634, and 646 displayed evolution in multi-drug resistance that most often worsened over time, but occasionally drugs with prior resistance regained sensitivity (FIGS. 5A-5G). Altogether, the resistance progressively developed as expected over time. Occasional examples of surprising drug sensitivity were observed for Dex and Cy that would have been difficult to predict clinically, and it appears that resistance to those agents may reverse over the disease course. For patients with samples available at multiple timepoints, PIs and IMiD resistance were always progressive and were not observed to reverse.

Example 3—Ex Vivo Drug Sensitivity of Daratumumab

Figure 6A:
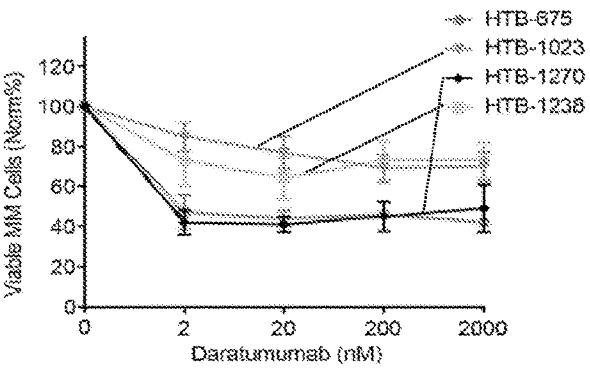
FIGS. 6A-6E show ex vivo drug sensitivity testing with the monoclonal antibody daratumumab.
Figure 6B:
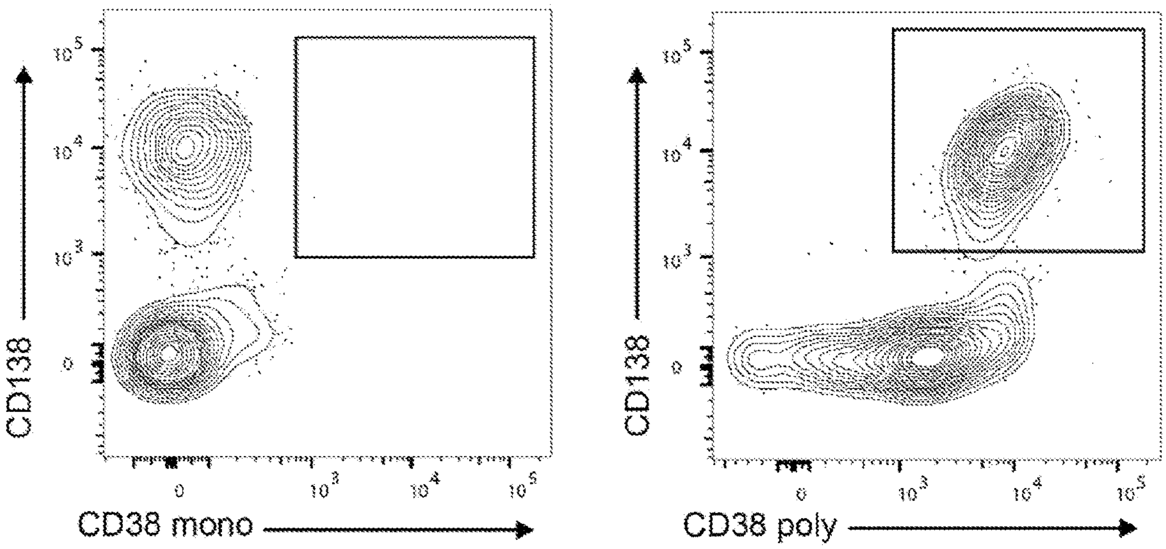
Figure 6C:
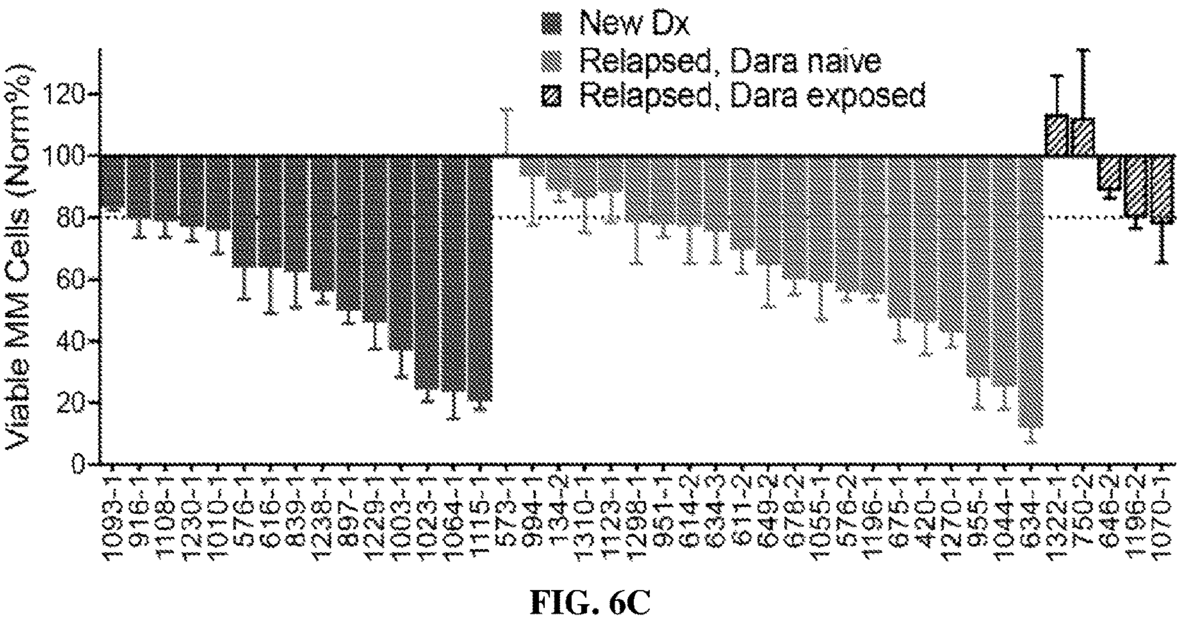
Figure 6D:
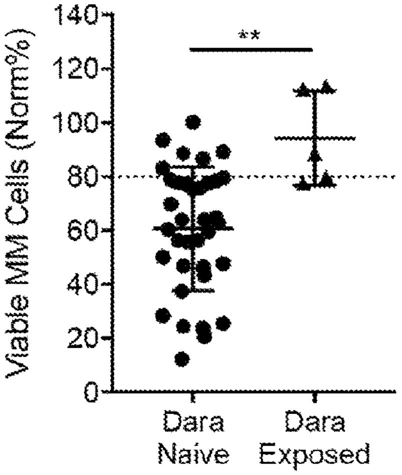
Figure 6E:
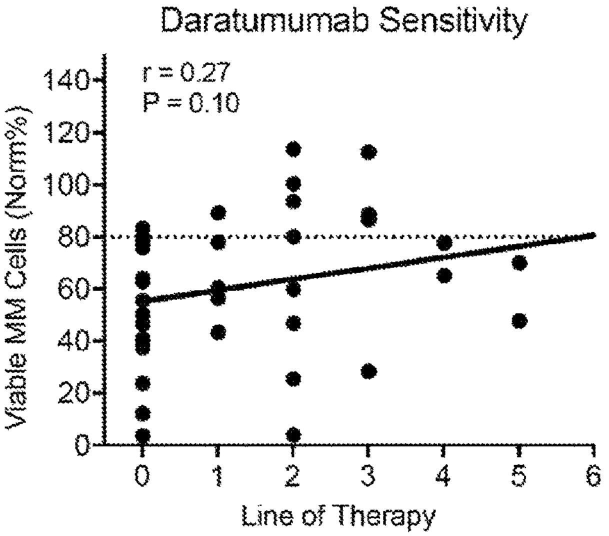

When drug resistance develops to both PIs and IMiDs, other drugs become critical as salvage therapy. Daratumumab ("Dara") has emerged in recent years as extremely valuable in this setting. Dara may be difficult to assay ex vivo, since its activity is at least partially due to monocyte antibody-dependent cellular cytotoxicity (ADCC) not captured in CD138-selected cell cultures. To test whether the activity of Dara could be assayed ex vivo in MNC cultures and if they retained activity in previously Dara-treated patients, the dose response to Dara was first measured, and 20 nM was chosen for single concentration screening (FIG. 6A). Because it was added later, Dara was tested on part of the cohort described above, totaling 15 from newly diagnosed, 21 relapsed, Dara-naïve and 5 relapsed, Dara-exposed patient samples. In samples from Dara-exposed patients, polyclonal anti-CD38 antibody was used to prevent antigen masking (FIG. 6B). Dara showed very similar activity in newly diagnosed and relapsed samples from Dara-naïve patients, but ex vivo resistance was evident in patients who had recently received Dara (FIG. 6C). Overall, the ex vivo sensitivity to Dara was significantly lower in naïve patients compared to those with prior exposure (P=0.003) (FIG. 6D). Ex vivo resistance to Dara displayed a nonsignificant correlation with increasing line of therapy (r=0.27, P=0.10), likely due to low number of samples from patients with prior exposure (FIG. 6E). In total, these findings demonstrate Dara activity can be measured in MNC cultures ex vivo, and activity is significantly diminished in patients that have developed clinical Dara resistance.

Figure 7A:
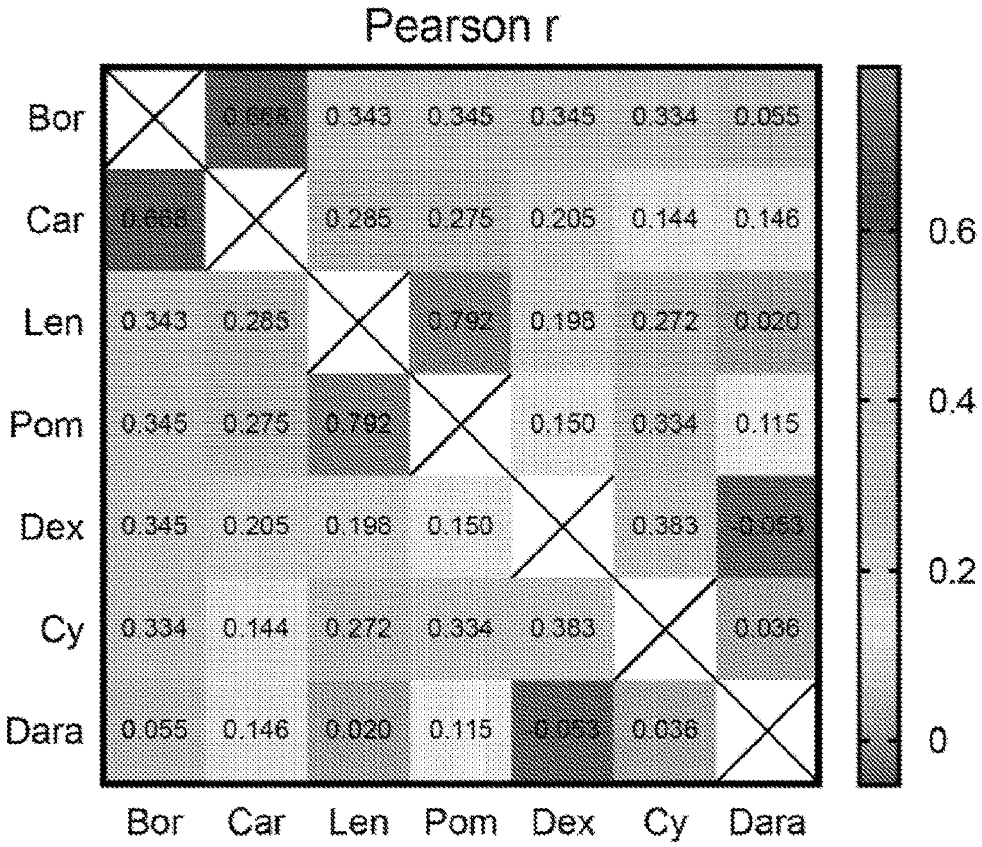
FIGS. 7A-7F show that ex vivo sensitivity results with daratumumab are related to its underlying mechanism of action.
Figure 7B:
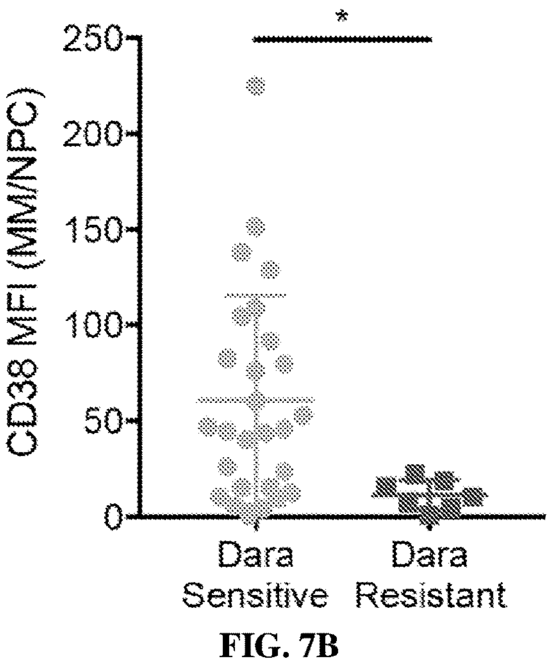
Figure 7C:
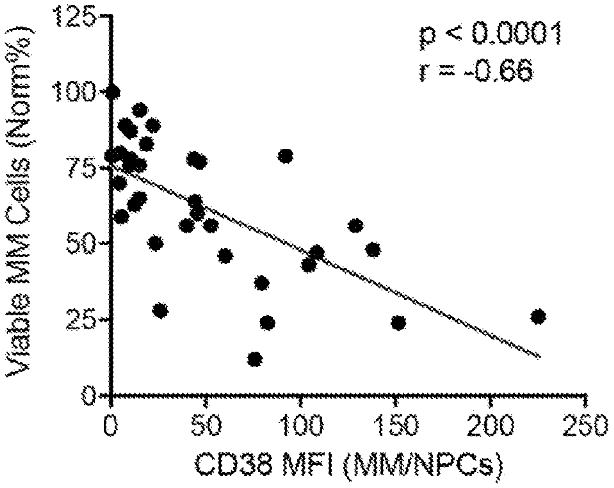
Figure 7D:
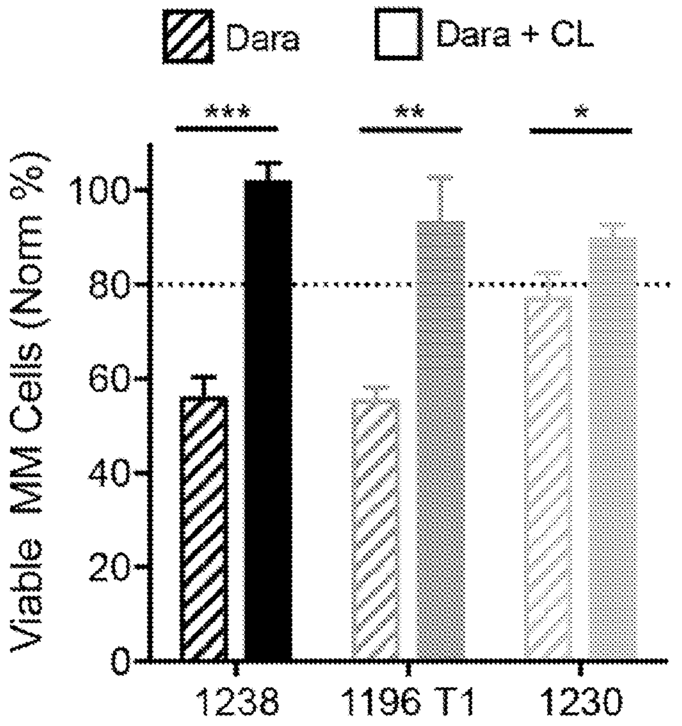
Figure 7E:
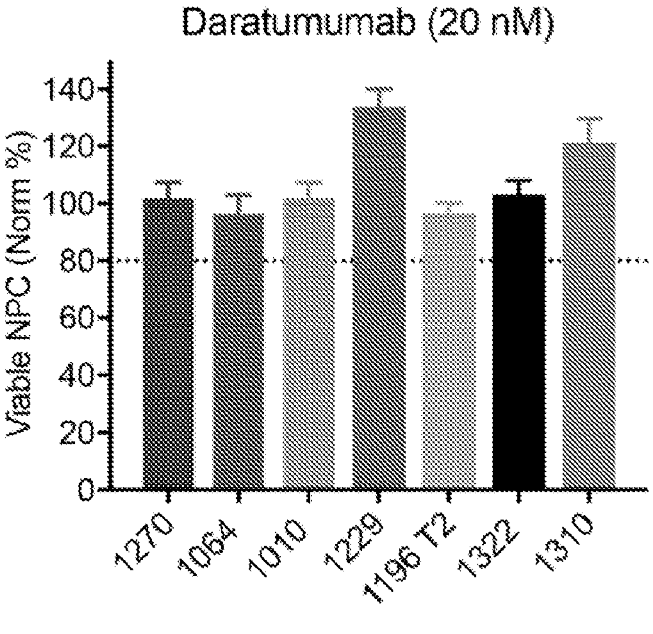
Figure 7F:
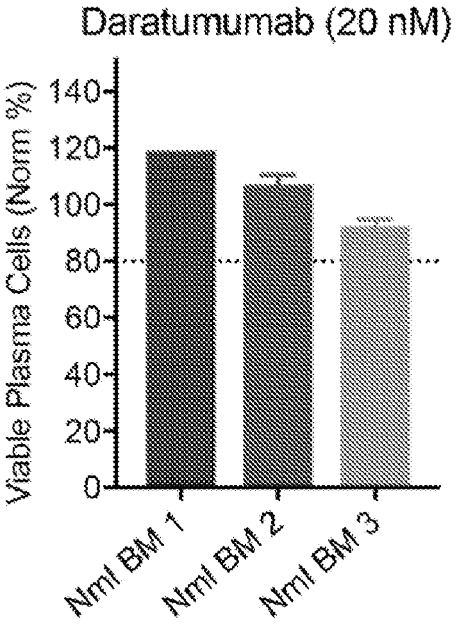

Consistent with its unique mechanism among the anti-myeloma therapies tested, Dara showed no correlation with the other drugs tested in myeloma drug sensitivity testing (My-DST) (FIG. 7A). Dara response has been reported to correlate with the level of MM cell CD38 expression, and consistent with this, CD38 expression was significantly lower in Dara-resistant samples, and sensitivity correlated with the CD38 median fluorescence intensity (FIGS. 7B and 7C). In 3/3 Dara-sensitive samples, the ex vivo activity was partially blocked by the addition of clodronate-containing liposomes to abolish macrophage antibody-dependent cellular phagocytosis (ADCP) (FIG. 7D). Lastly, no off-target effect on NPC in MNC cultures was observed, or on nonmalignant plasma cells from normal donor bone marrow (FIG. 7E-F). Thus, ex vivo Dara activity is correlated CD38-target expression and macrophage-dependent cytotoxicity, known biomarkers of its clinical activity.

Example 4—Correlation of Ex Vivo Sensitivity to Prior Clinical Drug Exposure

Figure 8A:
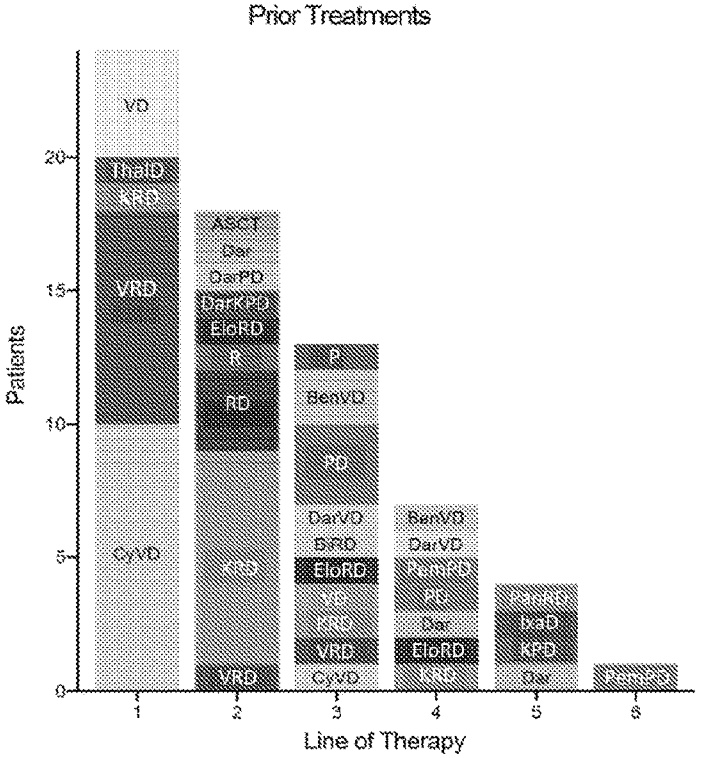
FIGS. 8A-8F show that prior clinical drug exposure results in decreased ex vivo myeloma drug sensitivity for proteasome inhibitors and immunomodulatory drugs, but no change in dexamethasone or cyclophosphamide sensitivity.
Figure 8B:
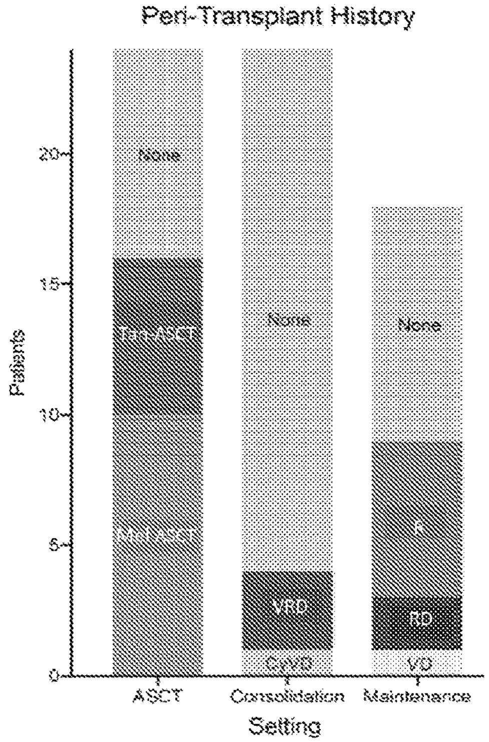
Figure 8C:
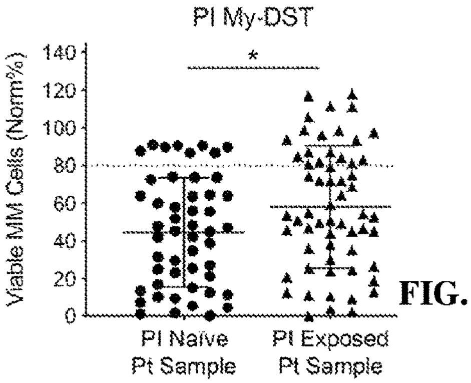
Figure 8D:
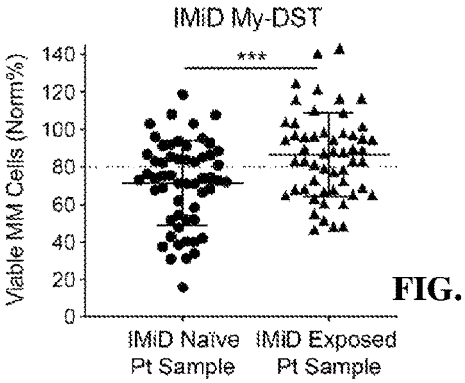
Figure 8E:
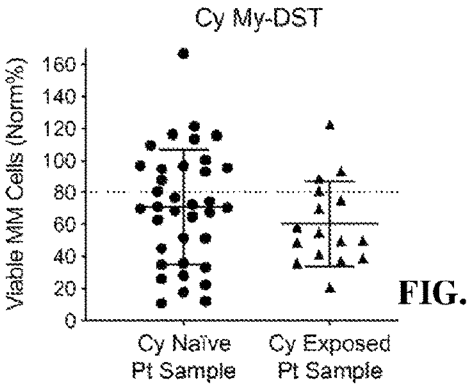
Figure 8F:
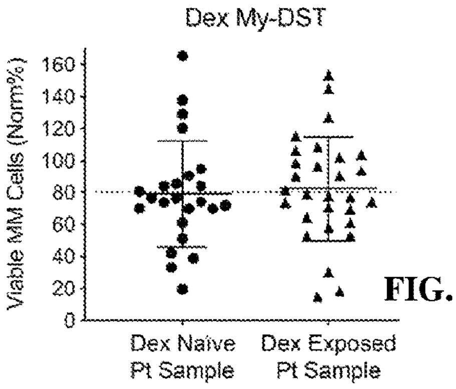

To further evaluate drug resistance found ex vivo, we next considered prior drug exposures of the samples. The treatment histories of the relapsed patients were diverse, but 1" line treatment included PI in 23/24, IMiD in 12/24 and Cy in 10/24. Most subsequent lines of therapies also included IMiDs and/or PIs (FIGS. 8A-8B) Therefore, we categorized drug sensitivity results by prior treatment history to the relevant agents. Importantly, sensitivity to both IMiDs and PIs were significantly lower in samples from patients who had previously received treatment with those classes (p=0.0007 and p=0.037, respectively) (FIGS. 8C-8D). In contrast, EV sensitivity to Dex and Cy were unchanged in samples with prior clinical exposure (FIGS. 8E-8F). Thus, the clinical PI and IMiD treatment of the patients affected their EV drug sensitivity, capturing the clinical context.

Example 5—Sensitivity and Specificity of Ex Vivo Drug Sensitivity

Figure 9A:
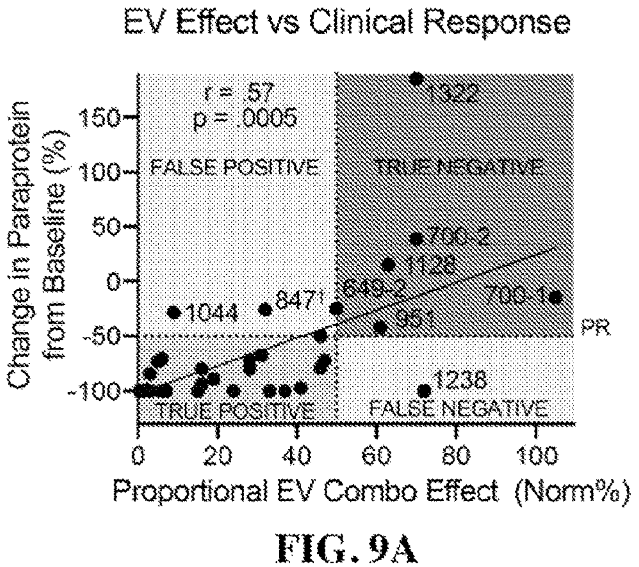
FIGS. 9A-9E show the clinical response correlations with ex vivo drug sensitivity results.

To assess the clinical impact of sensitivity to individual agents comprising the subsequent LOT, patient outcomes after My-DST were measured. Only patients subsequently treated exclusively with drugs tested in My-DST were included in these analyses (Table 1), patients who received other drugs were excluded. First, how pretreatment My-DST results compared to depth of subsequent clinical response was assessed by the change in MM-specific paraprotein by International Myeloma Working Group (IMWG) criteria after 4 treatment cycles. The cumulative proportional effect of the drugs received clinically was calculated by taking the product of the individual EV drug effects (Table 1). This My-DST combo effect correlated strongly with the depth of clinical response (r=0.57, p=0.0005) (FIG. 9A). Using a clinical response cutoff of −50% (PR) or better, a combo effect cutoff of ≤50% was 96% sensitive (23 true positive, 1 false negative) and 75% specific (6 true negative, 2 false positive). Thus, although drug synergy was not accounted for in the current design, My-DST was still sensitive for response and specific for identification of drug resistance.

TABLE 1

Comparison of ex vivo results to clinical outcomes for patients treated with agents tested in myeloma-drug sensitivity testing (My-DST).

| Pt # | HR | Prior Treatment Lines | MyDST of Drugs in Next LOT (Norm %) | MyDST Comb | Drugs Sens | Clinical Resp |
|---|---|---|---|---|---|---|
| 134 | 1q+ | none | V 5 D 129 | 6 | 1 | −71 |
| 576-1 | none | none | V 35 C 116 D 70 | 28 | 2 | −72 |
| 616 | none | none | V 2 C 88 D 19 | 0.3 | 2 | −100 |
| 656 | 1q+ | none | V 13 C 45 D 51 | 3 | 3 | −100 |
| 748 | none | none | V 45 C 67 D 81 | 24 | 2 | −100 |
| 820 | 1q+ | none | V 56 R 16 D 165 | 15 | 2 | −100 |
| 829 | none | none | V 89 R 74 D 70 | 46 | 2 | −79 |
| 839 | none | none | V 47 C 113 D 70 | 37 | 2 | −100 |
| 847* | none | none | R 81 D 39 | 32 | 1 | −26 |
| 854 | t(4;14) | none | V 7 C 65 D 42 | 2 | 3 | −99 |
| 897 | none | none | V 46 C 72 D 84 | 28 | 2 | −78 |
| 1003 | 1q+ | none | V 14 C 63 D 84 | 7 | 2 | −100 |
| 1023 | 1q+ | none | V 73 R 76 D 74 | 41 | 3 | −97 |
| 1064 | none | none | V 10 C 26 D 33 | 1 | 3 | −100 |
| 1093 | 1q+ | none | V 52 C 103 R 36 D 85 | 16 | 2 | −80 |
| 1115 | none | none | V 90 R 71 D 74 | 47 | 2 | −72 |
| 1128 | None | none | V 64 C 110 D 90 | 63 | 1 | +15 |
| 1229 | none | none | V 48 R 73 D 95 | 33 | 2 | −100 |
| 1230 | 1q+ | none | V 25 R 93 D 70 | 16 | 2 | −94 |
| 1238 | none | none | V 56 R 94 D 138 | 72 | 2 | −100 |
| 700-1 | 1q+ | VCD/SCT | R 73 D 145 | 105 | 1 | −15 |
| 951 | none | VRD/Mul/tSCT/ cRVD/mRD | Dar 78 D 79 | 61 | 2 | −42 |
| 1270 | 1q+ | KRD/SCT/mR | Dar 43 V 13 D 53 | 3 | 3 | −16 |
| 573 | 1q+ | VRD/Mul/SCT/ mR, KRD | C 71 P 68 D 58 | 28 | 3 | −80 |
| 700-2 | 1q+ | VCD/SCT/Ob/RD | V 87 D 81 | 70 | 0 | +38 |
| 1044 | 1q+ | VRD/SCT/cVRD/ mVD, EloRD/Obs | Dar 26 P 67 D 53 | 9 | 3 | −28.5 |
| 1322 | none | VRD, DarPD | Dar 114 V 72 P 88 D 97 | 70 | 1 | +185 |
| 955 | 1q+ | Unk/Mul/SCT/mRD/ Obs, RD, KRD | P 65 D 71 | 46 | 2 | −50 |
| 614-2 | 1q+ | VCD/Mul/KRD/SCT/ cVRD, EloRD, PD | Dar 78 V 27 D 90 | 19 | 2 | −89 |
| 649-2 | none | VCD, KRD/SCT/ mR, BiRD, PemPD | Dar 65 V 82 D 94 | 50 | 1 | −25 |
| 634-3 | none | VD/SCT, RD, VD, KD, ID, PemPD | Dar 76 V 47 D 15 | 5 | 3 | −73 |

MyDST of Drugs Received in Next LOT - ex vivo effects of the drugs subsequently received in clinical treatment (numbers represent the number of viable MM cells normalized as percent of untreated controls). MyDST Comb - the proportional ex vivo effect calculated the product of the individual mean effects for the drugs received in clinical treatment. Clinical Resp - clinical response shown as the percent change in paraprotein after 4 cycles.

*847 was treated with 2 cycles of RD, followed by switch to VD. Bi—Biaxin, c—consolidation, C—cyclophosphamide, Dar—daratumumab, D—dexamethasone, I—Ixazomib, K—carfilzomib, L—line, m—maintenance, Mul—multiple agent inpatient chemotherapy, Ob—observation, Pan—panobinostat, Pem—pembrolizumab, P—pomalidomide, R—Revlimid (lenalidomide), SCT—autologous stem cell transplant with melphalan, Unk—unknown, V—Velcade (bortezomib).

Figure 9B:
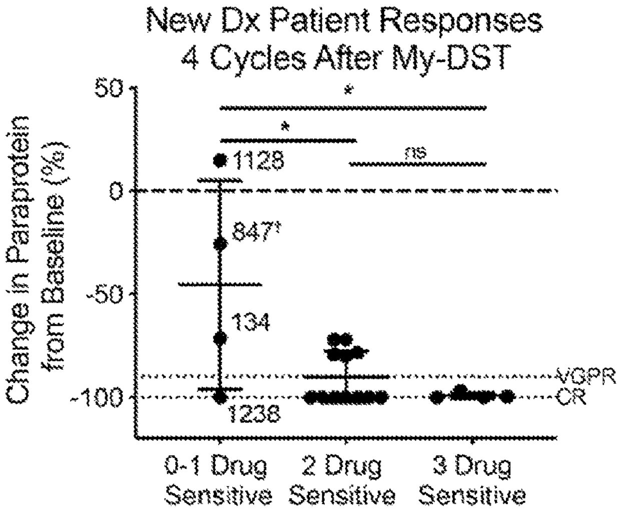
Figure 9C:
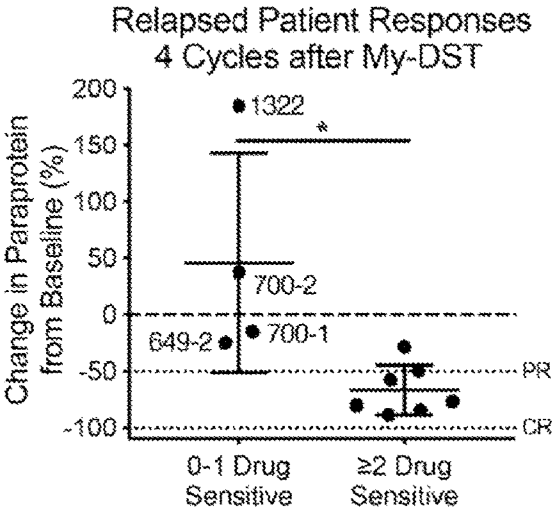
Figure 9D:
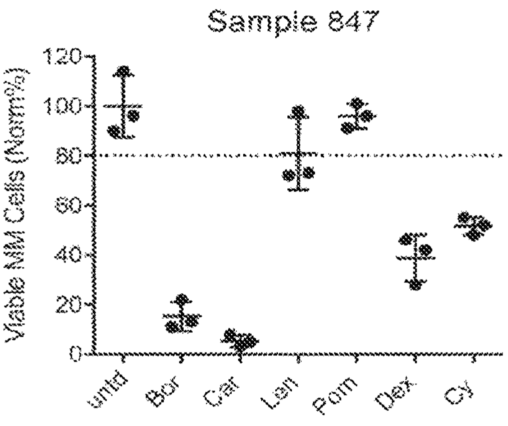
Figure 9E:
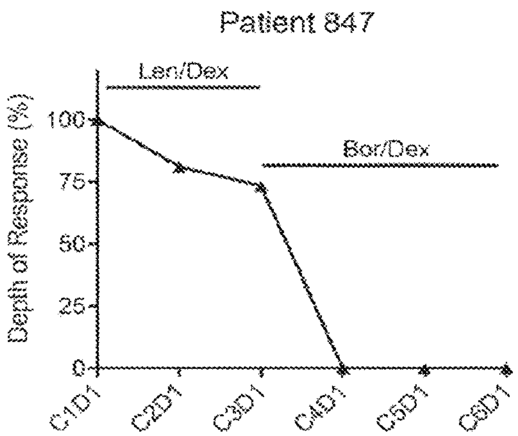

Example 6—Clinical Outcomes Correlate with Ex Vivo Drug Sensitivity Testing Results To assess whether sensitive vs. resistance scoring in these testing procedures was clinically meaningful, patient outcomes from treatment were examined retrospectively. In the upfront setting in this cohort, fit patients were treated with either the 3-drug combinations of Bor-Len-Dex or Cy-Bor-Dex, and frail patients were treated with 2-drug combinations of either Bor-Dex or Len-Dex. The depth of response was first examined. Patients at diagnosis treated with 3 drugs classified as sensitive EV reached complete response (CR, n=3) or very good partial response (VGPR, 90% decrease in paraprotein, n=1). Patients treated with 2 EV sensitive drugs achieved PR (n=4) or CR (n=7). In contrast, patients receiving only one EV sensitive drug had significantly less deep responses, with 3/4 patients achieving PR or less ex vivoex vivo (FIG. 9B). Similarly, relapsed patients receiving <1 EV sensitive drug predicted 4/5 patients who subsequently progressed or failed to achieve at least PR (FIG. 9C). As a specific example of potential clinical utility, the test for sample 847 at diagnosis identified sensitivity to PIs and inherent resistance to IMiDs (FIG. 9D). This correlated well with the patient's response judged by decrease in light chain levels relative to diagnosis showing inadequate response to lenalidomide and dexamethasone, followed by complete response after change in therapy to bortezomib and dexamethasone (FIG. 9E).

Figure 9F:
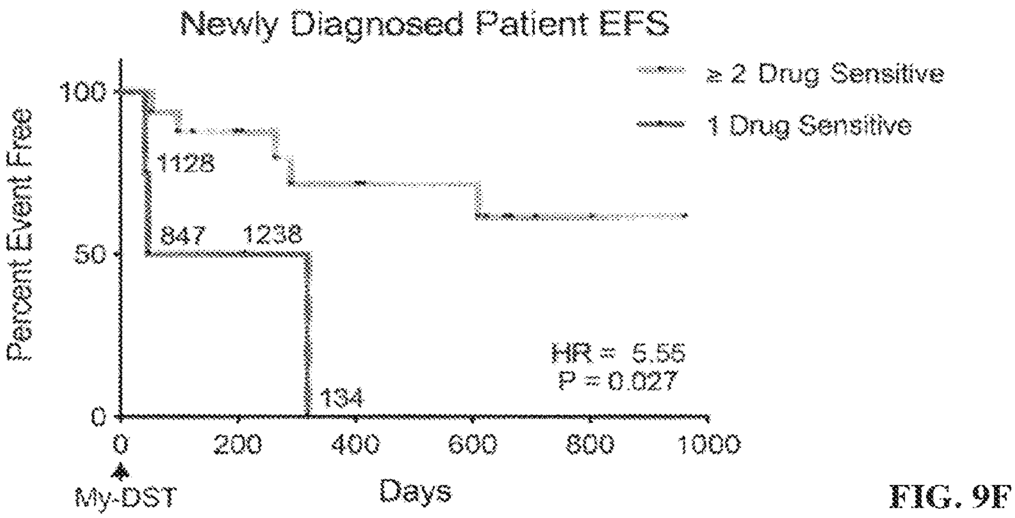
FIG. 9F shows that EFS was significantly longer on post-My-DST treatment for newly diagnosed patients treated when patients received at least 2 EV sensitive drugs.
Figure 9G:
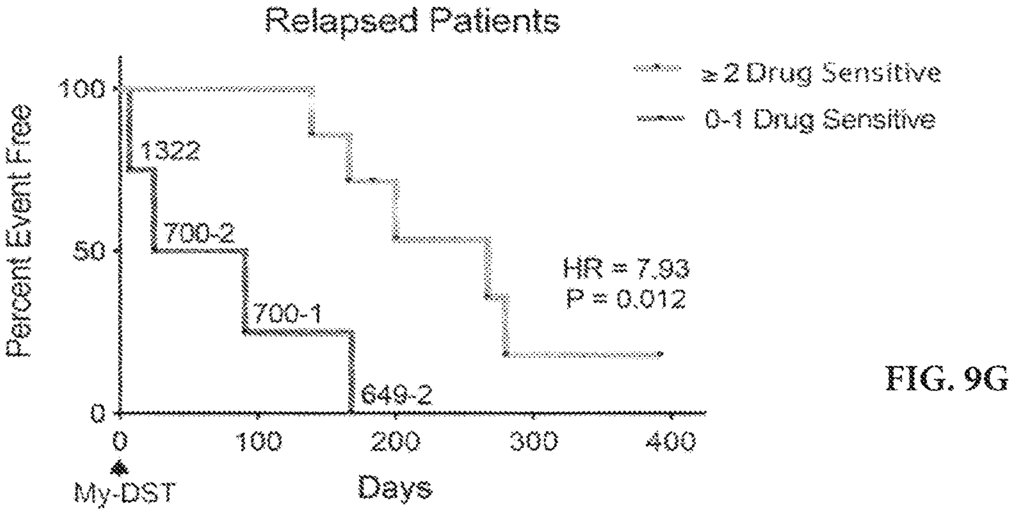
FIG. 9G shows that EFS on post-My-DST treatment was significantly longer in relapsed patients when patients received at least 2 EV sensitive drugs ex vivo.†—Clinical responses were measured after 4 subsequent treatment cycles, except for patient 847 who was assessed after 2 cycles due to subsequently changing treatment regimen. EFS data represent or time to progression or change in therapy due to inadequate response. Datapoints are labeled with sample numbers for patients with notably less ex vivo or clinical responses, whereas the others are removed for clarity. Data represent mean±SD, comparisons made with ANOVA (FIG. 9B), student's t-test (FIG. 9C) and Cox proportional hazard models to determine HR (FIGS. 9D-9E). *p<0.05, **p<0.01.

Next, how EV sensitivity influenced the subsequent event free survival (EFS) was examined, defined as time to progression or change in therapy due to inadequate response. The clinical characteristics of the newly diagnosed and relapsed cohorts are shown in Tables 2-3. Median follow-up for the newly diagnosed patients was 624 days (95% confidence interval [CI] 210-708) and 168 days for relapsed patients (95% CI 25-280). Newly diagnosed patients receiving only 1 EV sensitive drug had significantly shorter EFS by Cox regression than patients treated receiving ≥2 EV sensitive drugs (hazard ratio [HR] 5.55, 95% CI 1.22-25.32, p=0.027) ex vivo (FIG. 9F). A similar difference occurred in the relapsed setting, with significantly shorter EFS for patients who received 0 or 1 EV sensitive drug than patients receiving ≥2 EV sensitive drugs (HR 7.93, 95% CI 1.39-45.24, p=0.012) ex vivoex vivo (FIG. 9G). At this point, no difference in overall survival between these groups has yet been observed (data not shown). These differences indicate that ensuring patients receive ≥2 active drugs as identified by the methods described herein improves patient outcomes.

TABLE 2

Clinical characteristics of newly diagnosed myeloma patients studied for ex vivo drug sensitivity.

| Pt # | Dz State | BM MM % | ISS/ R-ISS | FISH | Next Line | Max Resp |
|---|---|---|---|---|---|---|
| 134-1 | Dx | 25 | I/II | 1q+, IgH+ | VD | PR |
| 576-1 | Dx | 40-50 | I/I | HD, 13q−, IgH+ | VCD | PR |
| 616 | Dx | 70-80 | III/II | t(11;14) | VCD | sCR |
| 656 | Dx | 10-25 | NA/≤II | 1q+ | VCD | CR |
| 748 | Dx | 10-15 | I/I | normal | VCD | CR |
| 766 | SMM | 15-20 | II/II | t(11;14) | none | NA |
| 820 | Dx | >95 | III/II | t(8;22), 1q+ | VRD | sCR |
| 829 | Dx | 70-80 | III/II | t(11;14) | VRD | VGPR |
| 839 | Dx | 20-25 | I/I | normal | VCD | CR |
| 847 | Dx | 15-20 | I/I | IgH+, 13q− | RD | MR |
| 854 | Dx | 80 | III/III | t(4;14) | VCD | CR |
| 897 | Dx | 5-7 | I/I | normal | VCD | PR |
| 916 | Dx | 80 | II/II | t(11;14) | none | NA |
| 1003 | Dx | 25-30 | II/II | 1q+, 13q−, IgH+ | VCD | CR |
| 1010 | Dx | 30 | I/≤II | normal | none | NA |
| 1023 | Dx | 40-60 | NA/≤II | t(11;14), 13q− | VRD | VGPR |
| 1064 | Dx | 15 | II/II | 13q− | VCD | CR |
| 1093 | Dx | 90 | III/III | t(8;14), 1q+, 13q− | VCD/VRD† | VGPR |
| 1115 | Dx | 70% | II/II | HD | VRD | PR |
| 1128 | Dx | 70-80 | III/II | HD | VCD | PD |
| 1229 | Dx | 40 | I/I | normal | VRD | VGPR |
| 1230 | Dx | 75 | II/II | HD, 1q+, 13q− | VRD | VGPR |
| 1238 | Dx | 50-70 | II/II | IgH+ | VRD | CR |
| 1298 | PCL | PB | II/II | N/A | none | NA |

†Treatment switched after first cycler due physician preference,
BM—bone marrow,
Bor—bortezomib,
Car—carfilzomib,
CR (complete response),
Cy—cyclophosphamide,
Dara—daratumumab,
D—dexamethasone,
DST-opt—drag sensitivity testing optimized,
Dx—diagnosis,
Dz—diagnosis,
Elo—elotuzumab,
HD—hyperdiploid,
IgH+—Uncharacterized IgH translocation,
Len—lenalidomide,
m—maintenance,
MR—minor response,
NA—not available,
Obs—observation,
Max Resp—maximum response,
Pan—panobinostat,
PB—peripheral blood sample,
PCL—plasma cell leukemia,
PD—progressive disease,
Pem—pembrolizumab,
Pom—pomalidomide,
PR—partial response,
SMM—smoldering multiple myeloma,
sCR—stringent complete response,
Tx—treatment,
VGPR—very good partial response

TABLE 3

Characteristics of relapsed multiple myeloma patients studied with ex vivo drug sensitivity testing.

| Pt # | Prior LOT | BM MM % | ISS/ R-ISS | FISH | Prior Treatment | Next Line |
|---|---|---|---|---|---|---|
| 134-2 | 1 | 10 | I/II | IgH+, 1q+ | VD/SCT/Ob | IRD |
| 576-2 | 1 | 40 | I/I | HD, 13q− | VCD/SCT/Ob | ID |
| 678 | 1 | 1-2 | II/II | normal | VCD/Ob | mR |
| 700-1 | 1 | 20 | NA | t(11;14), 1q+ | VCD/ASCT/Ob | RD |
| 951 | 1 | 12 | III/II | t(11;14) | VRD/Mul/t-SCT/cVRD/mRD/Ob | DarD |
| 1270 | 1 | 80 | I/I | 1q+, 13q−, IgH+ | KRD/SCT/mR | DarVD |
| 420 | 2 | 15 | III/II | normal | VCD, KRD/SCT/mR | mR |

TABLE 3-continued

Characteristics of relapsed multiple myeloma patients studied with ex vivo drug sensitivity testing.

| Pt # | Prior LOT | BM MM % | ISS/ R-ISS | FISH | Prior Treatment | Next Line |
|---|---|---|---|---|---|---|
| 573 | 2 | 50-70 | III/II | t(11;14), 1q+, 13q− | VRD/Mul/SCT/mR, KRD | CyPD |
| 614-1 | 2 | 5-10 | I/I | HD, 13q−, 1q+, t(1;14) | VCD, Mul/KRD/SCT/cVRD | EloRD |
| 649-1 | 2 | 5-10 | II/II | HD, 1q+, 13− | VCD, KRD/SCT/mR | BiRD |
| 700-2 | 2 | 30 | NA | t(11;14), 1q+ | VCD/SCT/Ob, RD | VD |
| 875 | 2 | 20 | NA | normal | VRD/Mul/SCT/Ob | N/A |
| 994 | 2 | 12 | II/≤II | IgH+ | VCD, KRD/mVCD/Ob | DarID |
| 1044 | 2 | 70-75 | I/I | 1q+, 13q−, IgH+ | VRD/SCT/cVRD/mVD, EloRD/Ob | DarVPD |
| 1196 | 2 | 70 | II/II | 1q+, 17p−, t(11;14), t(8;14) | VLRD, DarKPD | Mul |
| 1322 | 2 | 5 | I/I | normal | VRD, DPD | DPVD |
| 750 | 3 | 70 | I/II | t(8;14), 17p−, 1q+, 13q− | VRD, mR, KD, Dar | Mul |
| 816 | 3 | 1 | II/≥II | HD, 17p−, 13q− | VCD/SCT, Mul/KRD, DarVD | Mul |
| 955 | 3 | 60-70 | III/≥II | 1q+ | NA/Mul/SCT/mRD/Ob, RD, KRD | PD |
| 1123 | 3 | 30 | NA | normal | ThalD, R, PD | IPD |
| 1310 | 3 | 50 | III/≥II | 1q+ | VCD, VRD, Ob, PD | Isa/Cem |
| 614-2 | 4 | 50 | I/I | HD, 1q+, 13q−, t(1;14) | VCD, Mul/KRD/SCT/cVRD, EloRD, PD | DarVD |
| 634-1 | 4 | 30-35 | NA | normal | VD/SCT, RD, VD, KD | ID |
| 646-1 | 4 | 40 | II/II | t(4;14), 1q+, 13q- | VD/Mul/SCT, KRD, BenRD, EloRD | DarD |
| 649-2 | 4 | 30-40 | II/II | HD, 13q− | VCD, KRD/SCT/mR, BiRD, PemPD | DarVD |
| 1070 | 4 | 20 | NA | 17p−, t(11;14) | VCD, KRD, PD, Dar | DarVD |
| 611 | 5 | 10-20 | NA/≤II | HD | VD, KRD, VCD, BenVD, KPD, mP | DarD |
| 634-2 | 5 | 50-60 | NA | normal | VD/SCT, RD, VD, KD, ID | PemPD |
| 646-2 | 5 | 80 | II/II | t(4;14), 1q+, 13− | VD/Mul/SCT, KRD, BenRD, EloRD, Dar | Mul |
| 675 | 5 | 90 | NA | t(11;14), 1q+ | VRD/SCT/mR, Mul/SCT, P, KRD, PanRD | PanRD |
| 634-3 | 6 | 50 | NA | normal | VD/SCT, RD, VD, KD, ID, PemPD | DarRD |

Ben—bendamustine Bi—biaxin, BM—bone marrow, c—consolidation, C—cyclophosphamide, Cem—cempilimab, Dar—daratumumab, D—dexamethasone, Elo—elotuzumab, I—Ixazomib, IgH+—Uncharacterized IgH translocation, Isa—isatuximab, K—Kyprolis (carfilzomib), m—maintenance, Mul—multiple agent inpatient chemotherapy, NA—not available, Ob—observation, Pan—panobinostat, Pem—pembrolizumab, P—pomalidomide, R—Revlimid (lenalidomide), SCT—autologous stem cell transplant with melphalan, Thal—thalidomide, V—Velcade (bortezomib).

Since the patient groups compared above were not pre-stratified, we also examined whether known poor prognostic factors could have skewed the analyses of drug sensitivity on clinical outcomes. In both diagnosis and relapsed settings, relevant characteristics were not significantly different between patients receiving 1 EV sensitive drug compared to those receiving ≥2 (Tables 4-5), indicating drug sensitivity was an independent factor in the poorer outcomes. Thus, overall My-DST identified lack of sensitivity to the individual agents when poor responses were observed, independent of conventional high risk factors, in both newly diagnosed and relapsed patients.

TABLE 4

Baseline disease and patient characteristics in the clinical outcomes correlation of newly diagnosed patients and My-DST results.

| Characteristic | Patients with EV Sensitivity to 1 Drug (n = 4) | Patients with EV Sensitivity to ≥2 Drugs (n = 16) | P value |
|---|---|---|---|
| Median Age (range), years | 58 (51-72) | 56.5 (41-73) | 0.46 (ns)‡ |
| ISS III | 25% | 35.7% | 1.0 (ns)† |
| R-ISS III | 0% | 12.5% | 1.0 (ns)† |
| High-Risk Cytogenetics | 0% | 6.7% | 1.0 (ns)† |
| Chromosome 1q gain | 25% | 31.2% | 1.0 (ns)† |

High-risk cytogenetics by IMWG criteria detected in our cohort included deletion of chromosome 17p, translocations t(4;14) and t(14;16). ISS—Multiple Myeloma International Staging System, R-ISS—Revised Multiple Myeloma International Staging System. P values were calculated using a two-tailed Fisher's exact test† or students t-test‡.

TABLE 5

Baseline disease and patient characteristics in the clinical outcomes correlation of relapsed patients and My-DST results.

| Characteristic | Patients with EV Sensitivity to 0-1 Drug (n = 4) | Patients with EV Sensitivity to ≥2 Drugs (n = 7) | P value |
|---|---|---|---|
| Median Age (range), years | 63 (51-64) | 62 (52-67) | 0.47 (ns)‡ |
| ISS III | 0% | 50% | 0.46 (ns)† |

TABLE 5-continued

Baseline disease and patient characteristics in the clinical outcomes correlation of relapsed patients and My-DST results.

| Characteristic | Patients with EV Sensitivity to 0-1 Drug (n = 4) | Patients with EV Sensitivity to ≥2 Drugs (n = 7) | P value |
|---|---|---|---|
| R-ISS III | 0% | 0% | 1.0 (ns)† |
| High-Risk Cytogenetics | 0% | 0% | 1.0 (ns)† |
| Chromosome 1q gain | 75% | 71.4% | 1.0 (ns)† |
| Median Prior LOT (range) | 3 (2-5) | 3 (2-6) | 0.27 (ns)‡ |
| IMiD Exposed | 75% | 85.7% | 1.0 (ns)† |
| IMiD Refractory | 75% | 57.1% | 1.0 (ns)† |
| PI Exposed | 100% | 100% | 1.0 (ns)† |
| PI Refractory | 50% | 57.1% | 1.0 (ns)† |

High-risk cytogenetics by IMWG criteria detected in our cohort included deletion of chromosome 17p, translocations t(4;14) and t(14;16). ISS—Multiple Myeloma International Staging System, R-ISS—Revised Multiple Myeloma International Staging System. P values were calculated using a two-tailed Fisher's exact test† or students t-test‡.

Example 10—Humanized Media Improves Myeloma Cell Ex Vivo Viability

Figure 10:
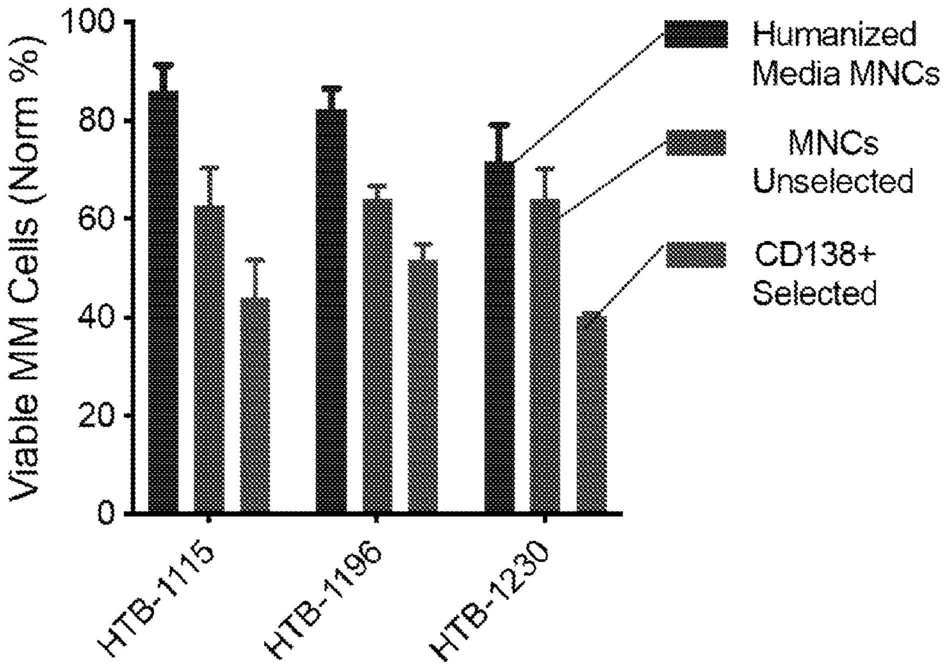
FIG. 10 shows that humanized media further improves ex vivo viability of human myeloma cells. Cell culture media with penicillin, streptomycin and IL6 addition were humanized by the manual addition of all 20 amino acids at concentrations representative to that of human plasma. Multiple myeloma patient samples were thawed and cultured in triplicate wells for 48 hours in this humanized media, compared to regular RPMI with penicillin, streptomycin and IL6, and CD138+ cell cultures that were purified via magnetic bead columns. The viability of the CD138+, CD38+ myeloma cells in the cultures was best in the humanized media cultures in 3/3 samples tested as judged by live/dead stain measured by multiparameter flow cytometry.

For more physiologic culture conditions better replicating human plasma, we synthesized a serum-free "humanized media" for My-DST. This humanized media contains (BIT 9500 Serum Substitute, StemCell Technologies) and LDL (Low-density lipoproteins, StemCell Technologies) to substitute for fetal bovine serum. Amino acids are added individually in concentrations replicating human plasma conditions (Table 6), which are considerably less than standard media. This improved the viability of the myeloma cells in My-DST in patient samples (FIG. 10).

TABLE 6

Amino acid composition of humanized media.

| Amino Acid | Final Conc (μM) |
|---|---|
| Alanine | 510.0 |
| L-Arginine | 64.0 |
| L-Asparagine | 41.0 |
| L-Cysteine | 65.0 |
| L-Glutamine | 410 μL of glutamax |
| Glycine | 330.0 |
| L-Histidine | 120.0 |
| L-Isoleucine | 140.0 |
| L-Leucine | 170.0 |
| Lysine | 220.0 |
| Methionine | 30.0 |
| Proline | 360.0 |
| Serine | 140.0 |
| Threonine | 240.0 |
| Tryptophan | 78.0 |
| Tyrosine | 74.0 |
| Valine | 230.0 |
| Phenylalanine | 68.0 |
| Aspartic Acid | 6.0 |
| Glutamic Acid | 98.0 |

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The term "or" is used in its inclusive sense so that when used, for example, to connect a list of elements, the term "or" means one, some, or all of the elements in the list.

Whereas certain example embodiments have been described, these embodiments have been presented by way of example only, and are not intended to limit the scope of the embodiments disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the embodiments disclosed herein. The accompanying claims and their equivalents are intended to cover such forms or modifications as would fall within the scope and spirit of certain of the embodiments disclosed herein.

What is claimed is:

1. A method for assessing sensitivity of multiple myeloma cells obtained from a subject to chemotherapeutic agents in an ex vivo assay, comprising:

obtaining multiple myeloma cells from a subject as part of cellular components of a bone marrow aspirate from the subject;

contacting the multiple myeloma cells obtained from the subject with at least one chemotherapeutic agent ex vivo for a period of 48 hours;

incubating the multiple myeloma cells with the at least one chemotherapeutic agent in a serum free media comprising low-density lipoproteins to which interleukin-6 (IL-6) has been added, to form incubated cells;

labeling at least one protein selected from the group consisting of CD138, CD38, CD45, and CD19, on the surface of the incubated cells to form labeled multiple myeloma (MM) cells; and analyzing the labeled MM cells by flow cytometry to determine the sensitivity and resistance of the subject's multiple myeloma cells to the at least one chemotherapeutic agent.

2. The method of claim 1, wherein the at least one chemotherapeutic agent includes a drug known to treat multiple myeloma in a subject.

3. The method of claim 1, wherein the at least one chemotherapeutic agent is selected from the group consisting of: an alkylating agent, an antimetabolite, a natural product, a hormone, a biologic, an antibody, a proteasome inhibitor, an immunomodulatory drug, a platinum coordination complex, and a histone deacetylase inhibitor.

4. The method of claim 1, wherein the at least one chemotherapeutic agent is selected from the group consisting of: bortezomib, carfilzomib, lenalidomide, pomalidomide, dexamethasone, cyclophosphamide, 4-hydroperoxy cyclophosphamide, and daratumumab.

5. The method of claim 1, wherein the incubating comprises incubating about $1\times10^2$ to $1\times10^8$ mononuclear cells from the subject.

6. The method of claim 1, wherein the incubating comprises incubating about $1\times10^4$ to $2\times10^5$ mononuclear cells from the subject.

7. The method of claim 1, wherein the incubation further comprises conditions to mimic human plasma nutrient concentrations of amino acids and lipids.

8. The method of claim 1, wherein the labeling comprises contacting the incubated cells with at least one antibody selected from the group consisting of: anti-CD19, anti-CD45, anti-CD38, and anti-CD138 antibodies.

9. The method of claim 1, wherein the analyzing comprises contacting the labeled multiple myeloma cells with a fluorescent dye that binds to free amines within the multiple myeloma cells and on the surface of the multiple myeloma cells resulting in less intense fluorescence from live multiple myeloma cells.

10. The method of claim 1, wherein the analyzing comprises gating the multiple myeloma cells on expression of one or more of CD38, CD138, CD19, and CD45.

11. The method of claim 1, wherein the analyzing comprises gating the multiple myeloma cells expressing clonal light chain restriction on CD19-CD45+/−CD38+CD138+.

12. The method of claim 1, wherein the analyzing comprises determining that the multiple myeloma cells from the subject are sensitive to the at least one chemotherapeutic agent when at least 20% cell death of the incubated multiple myeloma cells is detected.

13. The method of claim 1, wherein the analyzing comprises determining that the multiple myeloma cells from the subject are resistant to the at least one chemotherapeutic agent when less than 20% cell death of the incubated multiple myeloma cells is detected.

14. The method of claim 1, wherein the multiple myeloma cells are obtained from a subject at the time of initial diagnosis with multiple myeloma.

15. The method of claim 1, wherein the multiple myeloma cells are obtained from a subject at the time of first relapse of multiple myeloma.

16. The method of claim 1, wherein the multiple myeloma cells are obtained from a subject at the time of second or subsequent relapse of multiple myeloma.

17. The method of claim 1, further comprising treating multiple myeloma in the subject with at least one chemotherapeutic agent to which the subject's MM cells are identified to be sensitive, compared to the untreated control condition.

* * * * *